(12) United States Patent
Sirdeshpande et al.

(10) Patent No.: US 10,435,637 B1
(45) Date of Patent: Oct. 8, 2019

(54) HYDROMETHANATION OF A CARBONACEOUS FEEDSTOCK WITH IMPROVED CARBON UTILIZATION AND POWER GENERATION

(71) Applicant: GreatPoint Energy, Inc., Chicago, IL (US)

(72) Inventors: Avinash Sirdeshpande, Chicago, IL (US); Earl T. Robinson, Lakeland, FL (US); Pattabhi K. Raman, Kildeer, IL (US); Kenneth Keckler, Naperville, IL (US)

(73) Assignee: GreatPoint Energy, Inc., Chicago, IL (US)

( * ) Notice: Subject to any disclaimer, the term of this patent is extended or adjusted under 35 U.S.C. 154(b) by 0 days.

(21) Appl. No.: 16/224,396

(22) Filed: Dec. 18, 2018

(51) Int. Cl.
*C10J 3/16* (2006.01)
*C07C 2/84* (2006.01)
*C07C 9/04* (2006.01)
*C07C 4/02* (2006.01)
*C07C 4/06* (2006.01)

(52) U.S. Cl.
CPC .............. *C10J 3/16* (2013.01); *C07C 2/84* (2013.01); *C07C 9/04* (2013.01); *C07C 2523/04* (2013.01); *C10J 2300/0913* (2013.01); *C10J 2300/0966* (2013.01); *C10J 2300/1653* (2013.01); *C10J 2300/1662* (2013.01)

(58) Field of Classification Search
None
See application file for complete search history.

(56) References Cited

U.S. PATENT DOCUMENTS

| | | | |
|---|---|---|---|
| 2,605,215 | A | 7/1952 | Coghlan |
| 2,694,623 | A | 11/1954 | Welty, Jr. et al. |
| 2,791,549 | A | 5/1957 | Jahnig |
| 2,809,104 | A | 10/1957 | Strasser et al. |
| 2,813,126 | A | 11/1957 | Tierney |
| 2,860,959 | A | 11/1958 | Pettyjohn et al. |
| 2,886,405 | A | 5/1959 | Benson et al. |
| 3,034,848 | A | 5/1962 | King |
| 3,114,930 | A | 12/1963 | Oldham et al. |

(Continued)

FOREIGN PATENT DOCUMENTS

| | | |
|---|---|---|
| CA | 966660 | 4/1975 |
| CA | 996353 | 9/1976 |

(Continued)

OTHER PUBLICATIONS

U.S. Appl. No. 12/788,538, filed May 12, 2010, Robinson, et al.

(Continued)

*Primary Examiner* — Medhanit W Bahta
(74) *Attorney, Agent, or Firm* — McDonnell Boehnen Hulbert & Berghoff LLP

(57) ABSTRACT

The present invention relates generally to processes for hydromethanating a carbonaceous feedstock in a hydromethanation reactor to a methane-enriched raw product stream, and more specifically to processing of solid char by-product removed from the hydromethanation reactor to improve the carbon utilization and thermal efficiency and economics of the overall process by co-producing electric power and steam from the by-product char in addition to the end-product pipeline quality substitute natural gas.

14 Claims, 4 Drawing Sheets

(56) References Cited

U.S. PATENT DOCUMENTS

| | | |
|---|---|---|
| 3,164,330 A | 1/1965 | Neidl |
| 3,351,563 A | 11/1967 | Negra et al. |
| 3,435,590 A | 4/1969 | Smith |
| 3,531,917 A | 10/1970 | Grunewald et al. |
| 3,544,291 A | 12/1970 | Schlinger et al. |
| 3,594,985 A | 7/1971 | Ameen et al. |
| 3,615,300 A | 10/1971 | Holm et al. |
| 3,689,240 A | 9/1972 | Aldridge et al. |
| 3,740,193 A | 6/1973 | Aldridge et al. |
| 3,746,522 A | 7/1973 | Donath |
| 3,759,036 A | 9/1973 | White |
| 3,779,725 A | 12/1973 | Hegarty et al. |
| 3,814,725 A | 6/1974 | Zimmerman et al. |
| 3,817,725 A | 6/1974 | Sieg et al. |
| 3,828,474 A | 8/1974 | Quartulli |
| 3,833,327 A | 9/1974 | Pitzer et al. |
| 3,840,354 A | 10/1974 | Donath |
| 3,847,567 A | 11/1974 | Kalina et al. |
| 3,876,393 A | 4/1975 | Kasai et al. |
| 3,904,386 A | 9/1975 | Graboski et al. |
| 3,915,670 A | 10/1975 | Lacey et al. |
| 3,920,229 A | 11/1975 | Piggott |
| 3,929,431 A | 12/1975 | Koh et al. |
| 3,958,957 A | 5/1976 | Koh et al. |
| 3,966,875 A | 6/1976 | Bratzler et al. |
| 3,969,089 A | 7/1976 | Moss et al. |
| 3,971,639 A | 7/1976 | Matthews |
| 3,972,693 A | 8/1976 | Wiesner et al. |
| 3,975,168 A | 8/1976 | Gorbaty |
| 3,985,519 A | 10/1976 | Kalina et al. |
| 3,989,811 A | 11/1976 | Hill |
| 3,993,457 A | 11/1976 | Cahn et al. |
| 3,996,014 A | 12/1976 | Muller et al. |
| 3,998,607 A | 12/1976 | Wesswlhoft et al. |
| 3,999,607 A | 12/1976 | Pennington et al. |
| 4,005,994 A | 2/1977 | Feldmann |
| 4,005,996 A | 2/1977 | Hausberger et al. |
| 4,011,066 A | 3/1977 | Bratzler et al. |
| 4,017,272 A | 4/1977 | Anwer et al. |
| 4,021,370 A | 5/1977 | Harris et al. |
| 4,025,423 A | 5/1977 | Stonner et al. |
| 4,044,098 A | 8/1977 | Miller et al. |
| 4,046,523 A | 9/1977 | Kalina et al. |
| 4,052,176 A | 10/1977 | Child et al. |
| 4,053,554 A | 10/1977 | Reed et al. |
| 4,057,512 A | 11/1977 | Vadovic et al. |
| 4,069,304 A | 1/1978 | Starkovich et al. |
| 4,077,778 A | 3/1978 | Nahas et al. |
| 4,091,073 A | 5/1978 | Winkler |
| 4,092,125 A | 5/1978 | Stambaugh et al. |
| 4,094,650 A | 6/1978 | Koh et al. |
| 4,100,256 A | 7/1978 | Bozzelli et al. |
| 4,101,449 A | 7/1978 | Noda et al. |
| 4,104,201 A | 8/1978 | Banks et al. |
| 4,113,615 A | 9/1978 | Gorbaty |
| 4,116,996 A | 9/1978 | Huang |
| 4,118,204 A | 10/1978 | Eakman et al. |
| 4,152,119 A | 5/1979 | Schulz |
| 4,157,246 A | 6/1979 | Eakman et al. |
| 4,159,195 A | 6/1979 | Clavenna |
| 4,162,902 A | 7/1979 | Wiesner et al. |
| 4,173,465 A | 11/1979 | Meissner et al. |
| 4,189,307 A | 2/1980 | Marion |
| 4,192,652 A | 3/1980 | Smith |
| 4,193,771 A | 3/1980 | Sharp et al. |
| 4,193,772 A | 3/1980 | Sharp |
| 4,200,439 A | 4/1980 | Lang |
| 4,204,843 A | 5/1980 | Neavel |
| 4,211,538 A | 7/1980 | Eakman et al. |
| 4,211,669 A | 7/1980 | Eakman et al. |
| 4,219,338 A | 8/1980 | Wolfs et al. |
| 4,225,457 A | 9/1980 | Schulz |
| 4,235,044 A | 11/1980 | Cheung |
| 4,243,639 A | 1/1981 | Haas et al. |
| 4,249,471 A | 2/1981 | Gunnerman |
| 4,252,771 A | 2/1981 | Lagana et al. |
| 4,260,421 A | 4/1981 | Brown et al. |
| 4,265,868 A | 5/1981 | Kamody |
| 4,270,937 A | 6/1981 | Adler et al. |
| 4,272,255 A | 6/1981 | Coates |
| 4,280,817 A | 7/1981 | Chauhan et al. |
| 4,284,416 A | 8/1981 | Nahas |
| 4,292,048 A | 9/1981 | Wesselhoft et al. |
| 4,298,584 A | 11/1981 | Makrides |
| 4,315,753 A | 2/1982 | Bruckenstein et al. |
| 4,315,758 A | 2/1982 | Patel et al. |
| 4,318,712 A | 3/1982 | Lang et al. |
| 4,318,732 A | 3/1982 | Sawyer, Jr. |
| 4,322,222 A | 3/1982 | Sass |
| 4,330,305 A | 5/1982 | Kuessner et al. |
| 4,331,451 A | 5/1982 | Isogaya et al. |
| 4,334,893 A | 6/1982 | Lang |
| 4,336,034 A | 6/1982 | Lang et al. |
| 4,336,233 A | 6/1982 | Appl et al. |
| 4,344,486 A | 8/1982 | Parrish |
| 4,347,063 A | 8/1982 | Sherwood et al. |
| 4,348,486 A | 9/1982 | Calvin et al. |
| 4,348,487 A | 9/1982 | Goldstein et al. |
| 4,353,713 A | 10/1982 | Cheng |
| 4,365,975 A | 12/1982 | Williams et al. |
| 4,372,755 A | 2/1983 | Tolman et al. |
| 4,375,362 A | 3/1983 | Moss |
| 4,385,905 A | 5/1983 | Tucker |
| 4,397,656 A | 8/1983 | Ketkar |
| 4,400,182 A | 8/1983 | Davies et al. |
| 4,407,206 A | 10/1983 | Bartok et al. |
| 4,412,840 A | 11/1983 | Goksel |
| 4,425,139 A | 1/1984 | Schmidt et al. |
| 4,428,535 A | 1/1984 | Venetucci |
| 4,432,773 A | 2/1984 | Euker, Jr. et al. |
| 4,433,065 A | 2/1984 | Van Der Burgt et al. |
| 4,436,028 A | 3/1984 | Wilder |
| 4,436,531 A | 3/1984 | Estabrook et al. |
| 4,439,210 A | 3/1984 | Lancet |
| 4,443,415 A | 4/1984 | Queneau et al. |
| 4,444,568 A | 4/1984 | Beisswenger et al. |
| 4,459,138 A | 7/1984 | Soung |
| 4,462,814 A | 7/1984 | Holmes et al. |
| 4,466,828 A | 8/1984 | Tamai et al. |
| 4,468,231 A | 8/1984 | Bartok et al. |
| 4,475,924 A | 10/1984 | Meyer |
| 4,478,425 A | 10/1984 | Benko |
| 4,478,725 A | 10/1984 | Velling et al. |
| 4,482,529 A | 11/1984 | Chen et al. |
| 4,491,609 A | 1/1985 | Degel et al. |
| 4,497,784 A | 2/1985 | Diaz |
| 4,500,323 A | 2/1985 | Siegfried et al. |
| 4,505,881 A | 3/1985 | Diaz |
| 4,514,912 A | 3/1985 | Janusch et al. |
| 4,508,544 A | 4/1985 | Moss |
| 4,508,693 A | 4/1985 | Diaz |
| 4,515,604 A | 5/1985 | Eisenlohr et al. |
| 4,515,764 A | 5/1985 | Diaz |
| 4,524,050 A | 6/1985 | Chen et al. |
| 4,540,681 A | 9/1985 | Kustes et al. |
| 4,541,841 A | 9/1985 | Reinhardt |
| 4,551,155 A | 11/1985 | Wood et al. |
| 4,558,027 A | 12/1985 | McKee et al. |
| 4,572,826 A | 2/1986 | Moore |
| 4,594,140 A | 6/1986 | Cheng |
| 4,597,775 A | 7/1986 | Billimoria et al. |
| 4,597,776 A | 7/1986 | Ullman et al. |
| 4,604,105 A | 8/1986 | Aquino et al. |
| 4,609,388 A | 9/1986 | Adler et al. |
| 4,609,456 A | 9/1986 | Deschamps et al. |
| 4,617,027 A | 10/1986 | Lang |
| 4,619,864 A | 10/1986 | Hendrix et al. |
| 4,620,421 A | 11/1986 | Brown et al. |
| 4,661,237 A | 4/1987 | Kimura et al. |
| 4,668,428 A | 5/1987 | Najjar |
| 4,668,429 A | 5/1987 | Najjar |
| 4,675,035 A | 6/1987 | Apffel |
| 4,678,480 A | 7/1987 | Heinrich et al. |
| 4,682,986 A | 7/1987 | Lee et al. |

(56) References Cited

U.S. PATENT DOCUMENTS

| | | |
|---|---|---|
| 4,690,814 A | 9/1987 | Velenyi et al. |
| 4,699,632 A | 10/1987 | Babu et al. |
| 4,704,136 A | 11/1987 | Weston et al. |
| 4,720,289 A | 1/1988 | Vaugh et al. |
| 4,747,938 A | 5/1988 | Khan |
| H478 H | 6/1988 | Blytas |
| 4,781,731 A | 11/1988 | Schlinger |
| 4,790,251 A | 12/1988 | Vidt |
| 4,803,061 A | 2/1989 | Najjar et al. |
| 4,808,194 A | 2/1989 | Najjar et al. |
| 4,810,475 A | 3/1989 | Chu et al. |
| 4,822,935 A | 4/1989 | Scott |
| 4,848,983 A | 7/1989 | Tomita et al. |
| 4,852,996 A | 8/1989 | Knop et al. |
| 4,854,944 A | 8/1989 | Strong |
| 4,861,346 A | 8/1989 | Najjar et al. |
| 4,861,360 A | 8/1989 | Apffel |
| 4,872,886 A | 10/1989 | Henley et al. |
| 4,876,080 A | 10/1989 | Paulson |
| 4,892,567 A | 1/1990 | Yan |
| 4,960,450 A | 10/1990 | Schwarz et al. |
| 4,995,193 A | 2/1991 | Soga et al. |
| 4,999,030 A | 3/1991 | Skinner et al. |
| 5,017,282 A | 5/1991 | Delbianco et al. |
| 5,055,181 A | 10/1991 | Maa et al. |
| 5,057,294 A | 10/1991 | Sheth et al. |
| 5,059,406 A | 10/1991 | Sheth et al. |
| 5,093,094 A | 3/1992 | Van Kleeck et al. |
| 5,094,737 A | 3/1992 | Bearden, Jr. et al. |
| 5,132,007 A | 7/1992 | Meyer et al. |
| 5,223,173 A | 6/1993 | Jeffrey |
| 5,225,044 A | 7/1993 | Breu |
| 5,236,557 A | 8/1993 | Muller et al. |
| 5,242,470 A | 9/1993 | Salter et al. |
| 5,250,083 A | 10/1993 | Wolfenbarger et al. |
| 5,277,884 A | 1/1994 | Shinnar et al. |
| 5,354,345 A | 10/1994 | Nehls, Jr. |
| 5,435,940 A | 7/1995 | Doering et al. |
| 5,485,728 A | 1/1996 | Dickinson |
| 5,500,044 A | 3/1996 | Meade et al. |
| 5,505,746 A | 4/1996 | Chriswell et al. |
| 5,536,893 A | 7/1996 | Gudmundsson |
| 5,616,154 A | 4/1997 | Elliott et al. |
| 5,630,854 A | 5/1997 | Sealock, Jr. et al. |
| 5,635,147 A | 6/1997 | Herbert et al. |
| 5,641,327 A | 6/1997 | Leas |
| 5,660,807 A | 8/1997 | Forg et al. |
| 5,669,960 A | 9/1997 | Couche |
| 5,670,122 A | 9/1997 | Zamansky et al. |
| 5,720,785 A | 2/1998 | Baker |
| 5,733,515 A | 3/1998 | Doughty et al. |
| 5,769,165 A | 6/1998 | Bross et al. |
| 5,776,212 A | 7/1998 | Leas |
| 5,785,721 A | 7/1998 | Brooker |
| 5,788,724 A | 8/1998 | Carugati et al. |
| 5,865,898 A | 2/1999 | Holtzapple et al. |
| 5,855,631 A | 6/1999 | Leas |
| 5,968,465 A | 10/1999 | Koveal et al. |
| 6,013,158 A | 1/2000 | Wootten |
| 6,015,104 A | 1/2000 | Rich, Jr. |
| 6,028,234 A | 2/2000 | Heinemann et al. |
| 6,090,356 A | 7/2000 | Jahnke et al. |
| 6,132,478 A | 10/2000 | Tsurui et al. |
| 6,180,843 B1 | 1/2001 | Heinemann et al. |
| 6,187,465 B1 | 2/2001 | Galloway |
| 6,379,645 B1 | 4/2002 | Bucci et al. |
| 6,389,820 B1 | 5/2002 | Rogers et al. |
| 6,419,888 B1 | 7/2002 | Wyckoff |
| 6,506,349 B1 | 1/2003 | Khanmamedov |
| 6,506,361 B1 | 1/2003 | Machado et al. |
| 6,602,326 B2 | 8/2003 | Lee et al. |
| 6,641,625 B1 | 11/2003 | Clawson et al. |
| 6,653,516 B1 | 11/2003 | Yoshikawa et al. |
| 6,692,711 B2 | 2/2004 | Alexion et al. |
| 6,790,430 B1 | 9/2004 | Lackner et al. |
| 6,797,253 B2 | 9/2004 | Lyon |
| 6,808,543 B2 | 10/2004 | Paisley |
| 6,830,597 B1 | 12/2004 | Green |
| 6,841,279 B1 | 1/2005 | Foger et al. |
| 6,855,852 B1 | 2/2005 | Jackson et al. |
| 6,878,358 B2 | 4/2005 | Vosteen et al. |
| 6,894,183 B2 | 5/2005 | Choudhary et al. |
| 6,955,595 B2 | 10/2005 | Kim |
| 6,955,695 B2 | 10/2005 | Nahas |
| 6,969,494 B2 | 11/2005 | Herbst |
| 7,056,359 B1 | 6/2006 | Somerville et al. |
| 7,074,373 B1 | 7/2006 | Warren et al. |
| 7,118,720 B1 | 10/2006 | Mendelsohn et al. |
| 7,132,183 B2 | 11/2006 | Galloway |
| 7,168,488 B2 | 1/2007 | Olsvik et al. |
| 7,205,448 B2 | 4/2007 | Gajda et al. |
| 7,220,502 B2 | 5/2007 | Galloway |
| 7,309,383 B2 | 12/2007 | Beech, Jr. et al. |
| 7,481,275 B2 | 1/2009 | Olsvik et al. |
| 7,666,383 B2 | 2/2010 | Green |
| 7,758,663 B2 | 7/2010 | Rabovitser et al. |
| 7,897,126 B2 | 3/2011 | Rappas et al. |
| 7,901,644 B2 | 3/2011 | Rappas et al. |
| 7,922,782 B2 | 4/2011 | Sheth |
| 7,926,750 B2 | 4/2011 | Hauserman |
| 7,976,593 B2 | 7/2011 | Graham |
| 8,021,445 B2 | 9/2011 | Shaffer |
| 8,114,176 B2 | 2/2012 | Nahas |
| 8,114,177 B2 | 2/2012 | Hippo et al. |
| 8,123,827 B2 | 2/2012 | Robinson |
| 8,163,048 B2 | 4/2012 | Rappas et al. |
| 8,192,716 B2 | 6/2012 | Raman et al. |
| 8,202,913 B2 | 6/2012 | Robinson et al. |
| 8,268,899 B2 | 9/2012 | Robinson et al. |
| 8,286,901 B2 | 10/2012 | Rappas et al. |
| 8,297,542 B2 | 10/2012 | Rappas et al. |
| 8,328,890 B2 | 12/2012 | Reiling et al. |
| 8,349,039 B2 | 1/2013 | Robinson |
| 8,361,428 B2 | 1/2013 | Raman et al. |
| 8,366,795 B2 | 2/2013 | Raman et al. |
| 8,479,833 B2 | 7/2013 | Raman |
| 8,479,834 B2 | 7/2013 | Preston |
| 8,502,007 B2 | 8/2013 | Hippo et al. |
| 8,557,878 B2 | 10/2013 | Rappas et al. |
| 8,647,402 B2 | 2/2014 | Robinson et al. |
| 8,648,121 B2 | 2/2014 | Rappas et al. |
| 8,652,222 B2 | 2/2014 | Raman et al. |
| 8,652,696 B2 | 2/2014 | Sirdeshpande |
| 8,653,149 B2 | 2/2014 | Robinson et al. |
| 8,669,013 B2 | 3/2014 | Powell et al. |
| 8,709,113 B2 | 4/2014 | Raman et al. |
| 8,728,182 B2 | 5/2014 | Sirdeshpande et al. |
| 8,728,183 B2 | 5/2014 | Reiling et al. |
| 8,733,459 B2 | 5/2014 | Wallace |
| 8,734,547 B2 | 5/2014 | Rappas et al. |
| 8,734,548 B2 | 5/2014 | Rappas et al. |
| 8,748,687 B2 | 6/2014 | Sirdeshpande |
| 8,999,020 B2 | 4/2015 | Raman et al. |
| 9,012,524 B2 | 4/2015 | Robinson et al. |
| 9,034,058 B2 | 5/2015 | Robinson et al. |
| 9,034,061 B2 | 5/2015 | Robinson et al. |
| 9,127,221 B2 | 9/2015 | Sirdeshpande |
| 9,234,149 B2 | 1/2016 | Lau et al. |
| 9,273,260 B2 | 3/2016 | Robinson et al. |
| 9,328,920 B2 | 5/2016 | Sirdeshpande et al. |
| 9,353,322 B2 | 5/2016 | Raman et al. |
| 2002/0036086 A1 | 3/2002 | Minkkinen et al. |
| 2003/0009943 A1 | 1/2003 | Millet et al. |
| 2003/0070808 A1 | 4/2003 | Allison |
| 2003/0131582 A1 | 7/2003 | Anderson et al. |
| 2003/0167691 A1 | 9/2003 | Nahas |
| 2004/0020123 A1 | 2/2004 | Kimura et al. |
| 2004/0023086 A1 | 2/2004 | Su et al. |
| 2004/0055716 A1 | 3/2004 | Landalv et al. |
| 2004/0123601 A1 | 7/2004 | Fan |
| 2004/0180971 A1 | 9/2004 | Inoue et al. |
| 2004/0256116 A1 | 12/2004 | Olsvik et al. |
| 2005/0107648 A1 | 5/2005 | Kimura et al. |
| 2005/0137442 A1 | 6/2005 | Gajda et al. |

(56) References Cited

U.S. PATENT DOCUMENTS

| | | |
|---|---|---|
| 2005/0192362 A1 | 9/2005 | Rodriguez et al. |
| 2005/0274113 A1 | 12/2005 | Sekiai et al. |
| 2005/0287056 A1 | 12/2005 | Baker et al. |
| 2005/0288537 A1 | 12/2005 | Maund et al. |
| 2006/0120953 A1 | 6/2006 | Okuyama et al. |
| 2006/0149423 A1 | 7/2006 | Barnicki et al. |
| 2006/0228290 A1 | 10/2006 | Green |
| 2006/0233687 A1 | 10/2006 | Hojlund Nielsen |
| 2006/0265953 A1 | 11/2006 | Hobbs |
| 2007/0000177 A1 | 1/2007 | Hippo et al. |
| 2007/0051043 A1 | 3/2007 | Schingnitz |
| 2007/0083072 A1 | 4/2007 | Nahas |
| 2007/0149423 A1 | 6/2007 | Warr et al. |
| 2007/0180990 A1 | 8/2007 | Downs et al. |
| 2007/0186472 A1 | 8/2007 | Rabovister et al. |
| 2007/0220810 A1 | 9/2007 | Leveson et al. |
| 2007/0227729 A1 | 10/2007 | Zubrin et al. |
| 2007/0237696 A1 | 10/2007 | Payton |
| 2007/0277437 A1 | 12/2007 | Sheth |
| 2007/0282018 A1 | 12/2007 | Jenkins |
| 2008/0022586 A1 | 1/2008 | Gilbert et al. |
| 2008/0072495 A1 | 3/2008 | Waycuilis |
| 2008/0134888 A1 | 6/2008 | Chao et al. |
| 2008/0141591 A1 | 6/2008 | Kohl |
| 2008/0223046 A1 | 9/2008 | Yakobson et al. |
| 2009/0012188 A1 | 1/2009 | Rojey et al. |
| 2009/0048476 A1 | 2/2009 | Rappas et al. |
| 2009/0090055 A1 | 4/2009 | Ohtsuka |
| 2009/0090056 A1 | 4/2009 | Ohtsuka |
| 2009/0139851 A1 | 6/2009 | Freel |
| 2009/0165361 A1 | 7/2009 | Rappas et al. |
| 2009/0165376 A1 | 7/2009 | Lau et al. |
| 2009/0165379 A1 | 7/2009 | Rappas |
| 2009/0165380 A1 | 7/2009 | Lau et al. |
| 2009/0165381 A1 | 7/2009 | Robinson |
| 2009/0165382 A1 | 7/2009 | Rappas et al. |
| 2009/0165383 A1 | 7/2009 | Rappas et al. |
| 2009/0165384 A1 | 7/2009 | Lau et al. |
| 2009/0166588 A1 | 7/2009 | Spitz et al. |
| 2009/0169448 A1 | 7/2009 | Rappas et al. |
| 2009/0169449 A1 | 7/2009 | Rappas et al. |
| 2009/0170968 A1 | 7/2009 | Nahas et al. |
| 2009/0173079 A1 | 7/2009 | Wallace et al. |
| 2009/0217575 A1 | 9/2009 | Raman et al. |
| 2009/0217582 A1 | 9/2009 | May et al. |
| 2009/0217584 A1 | 9/2009 | Raman et al. |
| 2009/0217585 A1 | 9/2009 | Raman et al. |
| 2009/0217586 A1 | 9/2009 | Rappas et al. |
| 2009/0217587 A1 | 9/2009 | Raman et al. |
| 2009/0217588 A1 | 9/2009 | Hippo et al. |
| 2009/0217589 A1 | 9/2009 | Robinson |
| 2009/0217590 A1 | 9/2009 | Rappas et al. |
| 2009/0218424 A1 | 9/2009 | Hauserman |
| 2009/0220406 A1 | 9/2009 | Rahman |
| 2009/0229182 A1 | 9/2009 | Raman et al. |
| 2009/0235585 A1 | 9/2009 | Neels et al. |
| 2009/0236093 A1 | 9/2009 | Zubrin et al. |
| 2009/0246120 A1 | 10/2009 | Raman et al. |
| 2009/0259080 A1 | 10/2009 | Raman et al. |
| 2009/0260287 A1 | 10/2009 | Lau |
| 2009/0305093 A1 | 12/2009 | Biollaz et al. |
| 2009/0324458 A1 | 12/2009 | Robinson et al. |
| 2009/0324459 A1 | 12/2009 | Robinson et al. |
| 2009/0324460 A1 | 12/2009 | Robinson et al. |
| 2009/0324461 A1 | 12/2009 | Robinson et al. |
| 2009/0324462 A1 | 12/2009 | Robinson et al. |
| 2010/0005710 A1 | 1/2010 | Shaffer |
| 2010/0011658 A1 | 1/2010 | Bruso |
| 2010/0071235 A1 | 3/2010 | Pan et al. |
| 2010/0071262 A1 | 3/2010 | Robinson et al. |
| 2010/0074829 A1 | 3/2010 | Koss |
| 2010/0076235 A1 | 3/2010 | Reiling et al. |
| 2010/0120926 A1 | 5/2010 | Robinson et al. |
| 2010/0121125 A1 | 5/2010 | Hippo et al. |
| 2010/0159352 A1 | 6/2010 | Gelin et al. |
| 2010/0168494 A1 | 7/2010 | Rappas et al. |
| 2010/0168495 A1 | 7/2010 | Rappas et al. |
| 2010/0179232 A1 | 7/2010 | Robinson et al. |
| 2010/0270506 A1 | 10/2010 | Goetsch et al. |
| 2010/0287835 A1 | 11/2010 | Reiling et al. |
| 2010/0287836 A1 | 11/2010 | Robinson et al. |
| 2010/0292350 A1 | 11/2010 | Robinson et al. |
| 2011/0031439 A1 | 2/2011 | Sirdeshpande et al. |
| 2011/0062012 A1 | 3/2011 | Robinson |
| 2011/0062721 A1 | 3/2011 | Sirdeshpande et al. |
| 2011/0062722 A1 | 3/2011 | Sirdeshpande et al. |
| 2011/0064648 A1 | 3/2011 | Preston et al. |
| 2011/0088896 A1 | 4/2011 | Preston |
| 2011/0088897 A1 | 4/2011 | Raman |
| 2011/0089271 A1 | 4/2011 | Werner |
| 2011/0146978 A1 | 6/2011 | Perlman |
| 2011/0146979 A1 | 6/2011 | Wallace |
| 2011/0197501 A1 | 8/2011 | Taulbee |
| 2011/0207002 A1 | 8/2011 | Powell et al. |
| 2011/0217602 A1 | 9/2011 | Sirdeshpande |
| 2011/0262323 A1 | 10/2011 | Rappas et al. |
| 2012/0046510 A1 | 2/2012 | Sirdeshpande |
| 2012/0060417 A1 | 3/2012 | Raman et al. |
| 2012/0102836 A1 | 5/2012 | Raman et al. |
| 2012/0102837 A1 | 5/2012 | Raman et al. |
| 2012/0210635 A1 | 8/2012 | Edwards |
| 2012/0213680 A1* | 8/2012 | Rappas ............ C10J 3/00 423/62 |
| 2012/0271072 A1 | 10/2012 | Robinson et al. |
| 2012/0305848 A1 | 12/2012 | Sirdeshpande |
| 2013/0042824 A1 | 2/2013 | Sirdeshpande |
| 2013/0046124 A1 | 2/2013 | Sirdeshpande |
| 2013/0172640 A1 | 7/2013 | Robinson et al. |
| 2014/0090584 A1 | 4/2014 | Sirdeshpande et al. |
| 2014/0094636 A1 | 4/2014 | Robinson et al. |
| 2015/0166910 A1 | 6/2015 | Robinson et al. |
| 2015/0299588 A1 | 10/2015 | Spitz et al. |

FOREIGN PATENT DOCUMENTS

| | | |
|---|---|---|
| CA | 1003217 | 1/1977 |
| CA | 1041553 | 10/1978 |
| CA | 1106178 | 8/1981 |
| CA | 1 125 026 | 6/1982 |
| CA | 1187702 | 6/1985 |
| CA | 1282243 | 4/1991 |
| CA | 1299589 | 4/1992 |
| CA | 1332108 | 9/1994 |
| CA | 2 673 121 A1 | 6/2008 |
| CA | 2713642 | 7/2009 |
| CN | 1477090 | 2/2004 |
| CN | 1554569 A | 12/2004 |
| CN | 101028925 A | 9/2007 |
| CN | 101074397 A | 11/2007 |
| CN | 101555420 | 10/2009 |
| CN | 101745435 | 6/2010 |
| DE | 2 210 891 | 3/1972 |
| DE | 2210891 | 9/1972 |
| DE | 2852710 | 6/1980 |
| DE | 3422202 | 12/1985 |
| DE | 100610607 | 6/2002 |
| EA | 819 | 4/2000 |
| EP | 0024792 | 3/1981 |
| EP | 0007247 B1 | 11/1982 |
| EP | 0 067 580 | 12/1982 |
| EP | 102828 | 3/1984 |
| EP | 0 138 463 | 4/1985 |
| EP | 0 225 146 | 6/1987 |
| EP | 0 259 927 | 3/1988 |
| EP | 0473153 | 3/1992 |
| EP | 0 723 930 | 7/1996 |
| EP | 1 001 002 | 5/2000 |
| EP | 1 004 746 A1 | 5/2000 |
| EP | 1 136 542 A1 | 9/2001 |
| EP | 1 207 132 | 5/2002 |
| EP | 1 741 673 | 6/2006 |
| EP | 1768207 | 3/2007 |
| EP | 2058471 | 5/2009 |
| FR | 797 089 | 4/1936 |

(56) References Cited

FOREIGN PATENT DOCUMENTS

| | | |
|---|---|---|
| FR | 2 478 615 | 9/1981 |
| FR | 2906879 | 4/2008 |
| GB | 593910 | 10/1947 |
| GB | 640907 | 8/1950 |
| GB | 676615 | 7/1952 |
| GB | 701 131 | 12/1953 |
| GB | 760627 | 11/1956 |
| GB | 798741 | 7/1958 |
| GB | 820 257 | 9/1959 |
| GB | 996327 | 6/1965 |
| GB | 1033764 | 6/1966 |
| GB | 1328053 | 8/1973 |
| GB | 1448562 | 9/1976 |
| GB | 1453081 | 10/1976 |
| GB | 1467219 | 3/1977 |
| GB | 1467995 | 3/1977 |
| GB | 1 599 932 | 7/1977 |
| GB | 1554948 | 10/1979 |
| GB | 1560873 | 2/1980 |
| GB | 1595612 | 8/1981 |
| GB | 1595622 | 8/1981 |
| GB | 2078251 | 1/1982 |
| GB | 2154600 | 9/1985 |
| GB | 2455864 | 6/2009 |
| JP | S28-6633 | 12/1953 |
| JP | S35-11945 | 8/1960 |
| JP | 53-94305 | 8/1978 |
| JP | 53-111302 | 9/1978 |
| JP | 54020003 | 2/1979 |
| JP | 54-150402 | 11/1979 |
| JP | 55-12181 | 1/1980 |
| JP | 56-145982 | 11/1981 |
| JP | 56157493 | 12/1981 |
| JP | S58-27312 B2 | 6/1983 |
| JP | 60-35092 | 2/1985 |
| JP | 60-77938 | 5/1985 |
| JP | S61-44995 A | 3/1986 |
| JP | 62241991 | 10/1987 |
| JP | 62 257985 | 11/1987 |
| JP | 03115491 | 5/1991 |
| JP | 2000290659 | 10/2000 |
| JP | 2000290670 | 10/2000 |
| JP | 2002105467 | 4/2002 |
| JP | 2004-132689 | 4/2004 |
| JP | 2004292200 | 10/2004 |
| JP | 2004298818 | 10/2004 |
| JP | 2006 169476 A | 6/2006 |
| KR | 10-1073780 | 10/2011 |
| WO | 9641070 A1 | 12/1996 |
| WO | 2000/18681 | 4/2000 |
| WO | WO 2000/043468 | 7/2000 |
| WO | WO 2002/040768 | 5/2002 |
| WO | WO 2002/079355 | 10/2002 |
| WO | 2002/103157 | 12/2002 |
| WO | 2003/018958 | 3/2003 |
| WO | WO 2003/033624 | 4/2003 |
| WO | 2004/055322 A1 | 7/2004 |
| WO | 2004/055323 | 7/2004 |
| WO | WO 2004/072210 | 8/2004 |
| WO | WO 2006/031011 | 3/2006 |
| WO | WO 2007/005284 | 1/2007 |
| WO | WO 2007/047210 | 4/2007 |
| WO | 2007/068682 | 6/2007 |
| WO | 2007/077137 | 7/2007 |
| WO | 2007/077138 | 7/2007 |
| WO | 2007/083072 | 7/2007 |
| WO | WO 2007/076363 | 7/2007 |
| WO | WO 2007/128370 | 11/2007 |
| WO | 2007/143376 | 12/2007 |
| WO | WO 2007/143376 | 12/2007 |
| WO | 2008/055591 A2 | 5/2008 |
| WO | 2008/058636 | 5/2008 |
| WO | WO 2008/073889 | 6/2008 |
| WO | 2008/087154 | 7/2008 |
| WO | 2009/018053 | 2/2009 |
| WO | WO 2009/018053 | 2/2009 |
| WO | WO 2009/048723 | 4/2009 |
| WO | WO 2009/048724 | 4/2009 |
| WO | 2009/086408 A1 | 7/2009 |
| WO | WO 2009/086361 | 7/2009 |
| WO | WO 2009/086362 | 7/2009 |
| WO | WO 2009/086363 | 7/2009 |
| WO | WO 2009/086366 | 7/2009 |
| WO | WO 2009/086367 | 7/2009 |
| WO | WO 2009/086370 | 7/2009 |
| WO | WO 2009/086372 | 7/2009 |
| WO | WO 2009/086374 | 7/2009 |
| WO | WO 2009/086377 | 7/2009 |
| WO | WO 2009/086383 | 7/2009 |
| WO | WO 2009/086407 | 7/2009 |
| WO | WO 2009/086408 | 7/2009 |
| WO | WO 2009/111330 | 9/2009 |
| WO | WO 2009/111331 | 9/2009 |
| WO | WO 2009/111332 | 9/2009 |
| WO | WO 2009/111335 | 9/2009 |
| WO | WO 2009/111342 | 9/2009 |
| WO | WO 2009/111345 | 9/2009 |
| WO | WO 2009/124017 | 10/2009 |
| WO | WO 2009/124019 | 10/2009 |
| WO | WO 2009/158576 | 12/2009 |
| WO | WO 2009/158579 | 12/2009 |
| WO | WO 2009/158580 | 12/2009 |
| WO | WO 2009/158582 | 12/2009 |
| WO | WO 2009/158583 | 12/2009 |
| WO | WO 2010/033846 | 3/2010 |
| WO | WO 2010/033848 | 3/2010 |
| WO | WO 2010/033850 | 3/2010 |
| WO | WO 2010/033852 | 3/2010 |
| WO | WO 2010/048493 | 4/2010 |
| WO | WO 2010/078297 | 7/2010 |
| WO | WO 2010/078298 | 7/2010 |
| WO | 2010/132549 A2 | 11/2010 |
| WO | 2010/132551 | 11/2010 |
| WO | 2011/017630 A1 | 2/2011 |
| WO | 2011/029278 | 3/2011 |
| WO | 2011/029282 | 3/2011 |
| WO | 2011/029283 | 3/2011 |
| WO | 2011/029284 | 3/2011 |
| WO | 2011/029285 | 3/2011 |
| WO | 2011/034888 A1 | 3/2011 |
| WO | 2011/034889 A1 | 3/2011 |
| WO | 2011/034890 | 3/2011 |
| WO | 2011/034891 A1 | 3/2011 |
| WO | 2011/049858 A2 | 4/2011 |
| WO | 2011/049861 A2 | 4/2011 |
| WO | 2011/063608 | 6/2011 |
| WO | 2011/076994 A1 | 6/2011 |
| WO | 2011/084580 A2 | 7/2011 |
| WO | 2011/084581 A1 | 7/2011 |
| WO | 2011/106285 A1 | 9/2011 |
| WO | 2011/139694 A1 | 11/2011 |
| WO | 2011/150217 A2 | 12/2011 |
| WO | 2012/024369 | 2/2012 |
| WO | 2012/033997 A1 | 3/2012 |
| WO | 2012/061235 A1 | 5/2012 |
| WO | 2012/061238 A1 | 5/2012 |
| WO | 2012/116003 A1 | 8/2012 |
| WO | 2012/145497 A1 | 10/2012 |
| WO | 2012/166879 A1 | 12/2012 |
| WO | 2013/025808 A1 | 2/2013 |
| WO | 2013/025812 A1 | 2/2013 |
| WO | 2013/052553 A1 | 4/2013 |

OTHER PUBLICATIONS

U.S. Appl. No. 12/788,548, filed May 12, 2010, Robinson, et al.
U.S. Appl. No. 12/788,552, filed May 12, 2010, Robinson, et al.
Adsorption, http://en.wikipedia.org/wiki/Adsorption, pp. 1-8, Oct. 2, 2007.
Amine gas treating, http://en.wikipedia.org/wiki/Acid_gas_removal, pp. 1-4, [Accessed from the Internet on Nov. 1, 2007].
Coal, http://en.wikipedia.org/wiki/Coal_gasification, pp. 1-8, Oct. 29, 2007.

(56) References Cited

OTHER PUBLICATIONS

Coal Data: A Reference, Energy Information Administration, Office of Coal, Nuclear, Electric, and Alternate Fuels U.S. Department of Energy, DOE/EIA-0064(93), Feb. 1995.
Deepak Tandon, Dissertation Approval, "Low Temperature and Elevated Pressure Steam Gasification of Illinois Coal", Jun. 13, 1996.
Demibras, "Demineralization of Agricultural Residues by Water Leaching", *Energy Sources*, vol. 25, pp. 679-687, (2003).
Fluidized Bed Gasifiers, http://www.energyproducts.com/fluidized_bed_gasifiers.htm, pp. 1-5, [Accessed from the Internet on Jan. 6, 2007].
Gas separation, http://en.wikipedia.org/wiki/Gas_separation, pp. 1-2, Feb. 24, 2007.
Gasification, http://en.wikipedia.org/wiki/Gasification, pp. 1-6, [Accessed from the Internet on Nov. 6, 2007].
Gallagher Jr., et al., "Catalytic Coal Gasification for SNG Manufacture", *Energy Research*, vol. 4, pp. 137-147, (1980).
Heinemann, et al., "Fundamental and Exploratory Studies of Catalytic Steam Gasification of Carbonaceous Materials", Final Report Fiscal Years 1985-1994.
Jensen, et al. Removal of K and Cl by leaching of straw char, *Biomass and Bioenergy*, vol. 20, pp. 447-457, (2001).
Mengjie, et al., "A potential renewable energy resource development and utilization of biomass energy", http://www.fao.org.docrep/T4470E/t4470e0n.htm, pp. 1-8, [Accessed from the Internet on Jan. 24, 2008].
Meyers, et al. Fly Ash as A Construction Material for Highways, A Manual. Federal Highway Administration, Report No. FHWA-IP-76-16, Washington, DC, 1976, pp. 1-198.
Coal Bottom Ash/Boiler Slag, http://www.p2pays.org/ref/13/12842/cbabs2.htm, pp. 1-7, [Accessed from the Internet on Aug. 7, 2018].
Natural gas processing, http://en.wikipedia.org/wiki/Natural_gas_processing, pp. 1-4, [Accessed from the Internet on Nov. 1, 2007].
Natural Gas Processing: The Crucial Link Between Natural Gas Production and Its Transportation to Market. Energy Information Administration, Office of Oil and Gas; pp. 1-11, (2006).
Prins, et al., "Exergetic optimisation of a production process of Fischer-Tropsch fuels from biomass", *Fuel Processing Technology*, vol. 86, pp. 375-389, (2004).
Reboiler, http://en.wikipedia.org/wiki/Reboiler, pp. 1-4, [Accessed from the Internet on Jan. 14, 2008].
What is XPS?, http://www.nuance.northwestern.edu/KeckII/xps1.asp, pp. 1-2, [Accessed from the Internet on Jan. 31, 2008].
2.3 Types of gasifiers, http://www.fao.org/docrep/t0512e/T0512e0a.htm, pp. 1-6, [Accessed from the Internet on Nov. 6, 2007].
2.4 Gasification fuels, http://www.fao.org/docrep/t0512e/T0512e0b.htm#TopofPage, pp. 1-8, [Accessed from the Internet on Nov. 6, 2007].
2.5 Design of downdraught gasifiers, http://www.fao.org/docrep/t0512e/T0512e0c.htm#TopOfPage, pp. 1-8, [Accessed from the Internet on Nov. 6, 2007].
2.6 Gas cleaning and cooling, http://www.fao.org/docrep/t0512e0d.htm#TopOFPage, pp. 1-3, [Accessed from the Internet on Nov. 6, 2007].
Moulton, Lyle K. "Bottom Ash and Boiler Slag", *Proceedings of the Third International Ash Utilization Symposium*, U.S. Bureau of Mines, Information Circular No. 8640, Washington, DC, 1973.
A.G. Collot et al., "Co-pyrolysis and co-gasification of coal and biomass in bench-scale fixed-bed and fluidized bed reactors", (1999) Fuel 78, pp. 667-679.
Wenkui Zhu et al., "Catalytic gasification of char from co-pyrolysis of coal and biomass", (2008) Fuel Processing Technology, vol. 89, pp. 890-896.
Chiesa P. et al., "Co-Production of hydrogen, electricity and C02 from coal with commercially ready technology. Part A: Performance and emissions", (2005) International Journal of Hydrogen Energy, vol. 30, No. 7, pp. 747-767.
Brown et al., "Biomass-Derived Hydrogen From a Thermally Ballasted Gasifier", DOE Hydrogen Program Contractors' Review meeting, May 18-21, 2003, Center for Sustainable Environmental Technologies Iowa State University.
Brown et al., "Biomass-Derived Hydrogen From A thermally Ballasted Gasifier", Final Technical Report, Iowa State University, Aug. 2005.
Chiaramonte et al, "Upgrade Coke by Gasification", (1982) Hydrocarbon Processing, vol. 61 (9), pp. 255-257 (Abstract only).
Pipeline Rules of Thumb Handbook, Ed. E.W. McAllister, 2002. (Abstract only).
Classification of Coal Engineering Toolbox (to establish ash content of bituminous and anthracite coal) [Retrieved from the internet Nov. 12, 2018:<http://www.engineeringtoolbox.com/classification-coal-d_164.html>] (Dec. 21, 2007).
Fluidized Bed Gasifier—National Energy Technology Laboratory [Retrieved from the Internet Nov. 12, 2018: <https://www.netl.doe.gov/research/coal/energy-systems/gasification/gasifipedia/fluidizedbed>].
Moriyama, et al., "Upgrading of Low Rank Coal as Coal Water Slurry and its Utilization", Coal Preparation, 2005, vol. 25, pp. 193-210. (Abstract only).
Organic Chemical Technology, Jinmin Dou, pp. 75-77, Chemical Industry Press, ISBN 7-5025-8071-9, 1991.
Powder River Coal Company [Retrieved from the Internet Nov. 13, 2018:<URL:http://web.ccsd.k12.wy.us/mines/ PR/CoalTypes.html>].
Technology and Operation of Ethylene Apparatus, Songhan Wang, pp. 456, China Petrochemical Press Co., Ltd. (English language equivalent not available) (Document unavailable).
U.S. Department of Energy, National Energy Technology Laboratory Report titled "Detailed Coal Specifications" issued Jan. 2012. (Abstract only).
Asami, K., et al., "Highly Active Iron Catalysts from Ferric Chloride or the Steam Gasification of Brown Coal," ind. Eng. Chem. Res., vol. 32, No. 8, 1993, pp. 1631-1636.
Berger, R., et al., "High Temperature $CO_2$-Absorption: A Process Offering New Prospects in Fuel Chemistry," The Fifth International Symposium on Coal Combustion, Nov. 2003, Nanjing, China, pp. 547-549.
Brown et al., "Biomass-Derived Hydrogen From A Thermally Ballasted Gasifier," DOE Final Technical Report, Award No. DE-FC36-01GO11091, Aug. 2005, 197 pages.
Brown et al., "Biomass-Derived Hydrogen From A Thermally Ballasted Gasifier," DOE Hydrogen Program Contractors' Review Metting, Center for Sustainable Environmental Technologies, Iowa State University, May 21, 2003.
Coal Conversion Processes (Gasification), Encyclopedia of Chemical Technology, $4^{th}$ Edition, vol. 6, pp. 541-566.
Cohen, S.J., Project Manager, "Large Pilot Plant Alternatives for Scaleup of the Catalytic Coal Gasification Process," FE-2480-20, U.S. Dept. of Energy, Contract No., EX-76-C-01-2480, 1979.
Euker, Jr., C.A., Reitz, R.A., Program Managers, "Exxon Catalytic Coal-Gasification-Process Development Program," Exxon Research & Engineering Company, FE-2777-31, U.S. Dept. of Energy, Contract No. ET-78-C-01-2777, 1981.
Kalina, T., Nahas, N.C., Project Managers, "Exxon Catalaytic Coal Gasification Process Predevelopment Program," Exxon Research & Engineering Company, FE-2369-24, U.S. Dept. of Energy, Contract No., E(49-18)-2369, 1978.
Nahas, N.C., "Exxon Catalytic Coal Gasification Process—Fundamentals to Flowsheets," Fuel, vol. 62, No. 2, 1983, pp. 239-241.
Ohtsuka, Y. et al., "Highly Active Catalysts from Inexpensive Raw Materials for Coal Gasification," Catalysis Today, vol. 39, 1997, pp. 111-125.
Ohtsuka, Yasuo et al, "Steam Gasification of Low-Rank Coals with a Chlorine-Free Iron Catalyst from Ferric Chloride," Ind. Eng. Chem. Res., vol. 30, No. 8, 1991, pp. 1921-1926.
Ohtsuka, Yasuo et al., "Calcium Catalysed Steam Gasification of Yalourn Brown Coal," Fuel, vol. 65, 1986, pp. 1653-1657.
Ohtsuka, Yasuo, et al, "Iron-Catalyzed Gasification of Brown Coal at Low Temperatures," Energy & Fuels, vol. 1, No. 1, 1987, pp. 32-36.

(56) References Cited

OTHER PUBLICATIONS

Ohtsuka, Yasuo, et al., "Ion-Exchanged Calcium From Calcium Carbonate and Low-Rank Coals: High Catalytic Activity in Steam Gasification," Energy & Fuels 1996, 10, pp. 431-435.
Ohtsuka, Yasuo et al., "Steam Gasification of Coals with Calcium Hydroxide," Energy & Fuels, vol. 9, No. 6, 1995, pp. 1038-1042.
Pereira, P., et al., "Catalytic Steam Gasification of Coals," Energy & Fuels, vol. 6, No. 4, 1992, pp. 407-410.
Ruan Xiang-Quan, et al., "Effects of Catalysis on Gasification of Tatong Coal Char," Fuel, vol. 66, Apr. 1987, pp. 568-571.
Tandon, D., "Low Temperature and Elevated Pressure Steam Gasification of Illinois Coal," College of Engineering in the Graduate School, Southern Illinois university at Carbondale, Jun. 1996.
Gerdes, Kristin, et al., "Integrated Gasification Fuel Cell Performance and Cost Assessment," National Energy Technology Laboratory, U.S. Department of Energy, Mar. 27, 2009, pp. 1-26.
Ghosh, S., et al., "Energy Analysis of a Cogeneration Plant Using Coal Gasification and Solid Oxide Fuel Cell," Energy, 2006, vol. 31, No. 2-3, pp. 345-363.
Jeon, S.K., et al., "Characteristics of Steam Hydrogasification of Wood Using a Micro-Batch Reactor," Fuel, 2007, vol. 86, pp. 2817-2823.
Li, Mu, et al., "Design of Highly Efficient Coal-Based Integrated Gasification Fuel Cell Power Plants," Journal of Power Sources, 2010, vol. 195, pp. 5707-5718.
Prins, M.J., et al., "Exergetic Optimisation of a Production Process of Fischer-Tropsch Fuels from Biomass," Fuel Processing Technology, 2005, vol. 86, No. 4, pp. 375-389.
U.S. Appl. No. 13/484,918, filed May 31, 2012.
U.S. Appl. No. 13/402,022, filed Feb. 22, 2012.
U.S. Appl. No. 13/450,995, filed Apr. 19, 2012.

\* cited by examiner

HYDROMETHANATION OF A CARBONACEOUS FEEDSTOCK WITH IMPROVED CARBON UTILIZATION AND POWER GENERATION

CROSS-REFERENCE TO RELATED APPLICATION

This application is related to U.S. application Ser. No. 16/171,858, filed Oct. 26, 2018, entitled HYDROMETHANATION OF A CARBONACEOUS FEEDSTOCK WITH IMPROVED CARBON UTILIZATION), which is incorporated by reference herein for all purposes as if fully set forth below.

FIELD OF THE INVENTION

The present invention relates generally to processes for hydromethanating a carbonaceous feedstock in a hydromethanation reactor to a methane-enriched raw product stream, and more specifically to the processing of solid char by-product removed from the hydromethanation reactor to improve the carbon utilization and thermal efficiency of the overall process, generate power for internal use and export, and thereby lower the net costs of a pipeline quality substitute natural gas (SNG) end product.

BACKGROUND

In view of numerous factors such as higher energy prices and environmental concerns, the production of value-added products (such as pipeline-quality substitute natural gas, hydrogen, methanol, higher hydrocarbons, ammonia and electrical power) from lower-fuel-value carbonaceous feedstocks (such as petroleum coke, resids, asphaltenes, coal and biomass) is receiving renewed attention.

Such lower-fuel-value carbonaceous feedstocks can be gasified at elevated temperatures and pressures to produce a synthesis gas stream that can subsequently be converted to such value-added products.

One advantageous gasification process is hydromethanation, in which the carbonaceous feedstock is converted in a fluidized-bed hydromethanation reactor in the presence of a catalyst source and steam at moderately-elevated temperatures and pressures to directly produce a methane-enriched synthesis gas stream raw product. This is distinct from conventional gasification processes, such as those based on partial combustion/oxidation of a carbon source at highly-elevated temperatures and pressures (thermal gasification, typically non-catalytic), where a syngas (carbon monoxide+ hydrogen) is the primary product (little or no methane is directly produced), which can then be further processed to produce methane (via catalytic methanation, see reaction (III) below) or any number of other higher hydrocarbon products.

Hydromethanation processes and the conversion/utilization of the resulting methane-rich synthesis gas stream to produce value-added products are disclosed, for example, in U.S. Pat. Nos. 3,828,474, 3,958,957, 3,998,607, 4,057,512, 4,092,125, 4,094,650, 4,204,843, 4,243,639, 4,468,231, 4,500,323, 4,541,841, 4,551,155, 4,558,027, 4,604,105, 4,617,027, 4,609,456, 5,017,282, 5,055,181, 6,187,465, 6,790,430, 6,894,183, 6,955,695, US2003/0167691A1, US2006/0265953A1, US2007/0000177A1, US2007/0083072A1, US2007/0277437A1, US2009/0048476A1, US2009/0090056A1, US2009/0090055A1, US2009/0165383A1, US2009/0166588A1, US2009/0165379A1, US2009/0170968A1, US2009/0165380A1, US2009/0165381A1, US2009/0165361A1, US2009/0165382A1, US2009/0169449A1, US2009/0169448A1, US2009/0165376A1, US2009/0165384A1, US2009/0217582A1, US2009/0220406A1, US2009/0217590A1, US2009/0217586A1, US2009/0217588A1, US2009/0218424A1, US2009/0217589A1, US2009/0217575A1, US2009/0229182A1, US2009/0217587A1, US2009/0246120A1, US2009/0259080A1, US2009/0260287A1, US2009/0324458A1, US2009/0324459A1, US2009/0324460A1, US2009/0324461A1, US2009/0324462A1, US2010/0071235A1, US2010/0071262A1, US2010/0120926A1, US2010/0121125A1, US2010/0168494A1, US2010/0168495A1, US2010/0179232A1, US2010/0287835A1, US2010/0287836A1, US2010/0292350A1, US2011/0031439A1, US2011/0062012A1, US2011/0062721A1, US2011/0062722A1, US2011/0064648A1, US2011/0088896A1, US2011/0088897A1, US2011/0146978A1, US2011/0146979A1, US2011/0207002A1, US2011/0217602A1, US2011/0262323A1, US2012/0046510A1, US2012/0060417A1, US2012/0102836A1, US2012/0102837A1, US2012/0213680A1, US2012/0271072A1, US2012/0305848A1, US2013/0046124A1, US2013/0042824A1, US2013/0172640A1, US2014/0094636A1, WO2011/029278A1, WO2011/029282A1, WO2011/029283A1, WO2011/029284A1, WO2011/029285A1, WO2011/063608A1 and GB1599932, all of which are hereby incorporated by reference. See also Chiaramonte et al, "Upgrade Coke by Gasification", *Hydrocarbon Processing*, September 1982, pp. 255-257; and Kalina et al, "Exxon Catalytic Coal Gasification Process Predevelopment Program, Final Report", Exxon Research and Engineering Co., Baytown, TX, FE236924, December 1978, all of which are also hereby incorporated by reference.

The hydromethanation of a carbon source typically involves four theoretically separate reactions:

Steam carbon: $C+H_2O \rightarrow CO+H_2$     (I)

Water-gas shift: $CO+H_2O \rightarrow H_2+CO_2$     (II)

CO Methanation: $CO+3H_2 \rightarrow CH_4+H_2O$     (III)

Hydro-gasification: $2H_2+C \rightarrow CH_4$     (IV)

In the hydromethanation reaction, the first three reactions (I-III) predominate to result in the following overall net reaction:

$2C+2H_2O \rightarrow CH_4+CO_2$     (V)

The overall hydromethanation reaction is essentially thermally balanced; however, due to process heat losses and other energy requirements (such as required for evaporation of moisture entering the reactor with the feedstock), some heat must be added to maintain the thermal balance.

Referring to FIG. 1, in one variation of the hydromethanation process, required carbon monoxide, hydrogen and heat energy can also at least in part be generated in situ by feeding oxygen into the hydromethanation reactor. See, for example, previously incorporated US2010/0287835A1 and US2011/0062721A1, as well as commonly-owned US2012/0046510A1, US2012/0060417A1, US2012/0102836A1, US2012/0102837A1, US2013/0046124A1, US2013/0042824A1, US2013/0172640A1 and US2014/0094636A1, and US2010/0076235A1, which is hereby incorporated by reference. The following exothermic reactions will provide the heat energy to balance the heat losses from the reactor and the energy requirement of the steam carbon and other endothermic reactions:

The result is a "direct" methane-enriched raw product gas stream also containing substantial amounts of hydrogen, carbon monoxide and carbon dioxide which can, for example, be directly utilized as a medium BTU energy source, or can be processed to result in a variety of higher-value product streams such as pipeline-quality substitute natural gas, high-purity hydrogen, methanol, ammonia, higher hydrocarbons, carbon dioxide (for enhanced oil recovery and industrial uses) and electrical energy.

A char by-product stream is also produced in addition to the methane-enriched raw product gas stream. The solid char by-product contains unreacted carbon, entrained hydromethanation catalyst and other inorganic components of the carbonaceous feedstock. The by-product char may contain 20 wt % or more carbon depending on the feedstock composition and hydromethanation conditions.

This by-product char is periodically or continuously removed from the hydromethanation reactor, and typically sent to a catalyst recovery and recycle operation to improve economics and commercial viability of the overall process. The nature of catalyst components associated with the char extracted from a hydromethanation reactor and methods for their recovery are disclosed, for example, in previously incorporated US2007/0277437A1, US2009/0165383A1, US2009/0165382A1, US2009/0169449A1 and US2009/0169448A1, as well as commonly-owned US2011/0262323A1 and US2012/0213680A1. Catalyst recycle can be supplemented with makeup catalyst as needed, such as disclosed in previously incorporated US2009/0165384A1.

Catalyst recovery, and particularly catalyst recovery from high-ash char products, is often difficult to perform economically due to several factors, including the volume of by-product char material produced.

In addition, the residue of the char after catalyst recovery still contains a significant amount of carbon that is unconverted and is effectively removed from the process.

It would, therefore, be desirable to find a way to more completely and efficiently utilize the carbon in the char by-product from the hydromethanation reactor while reducing the volume of material that is ultimately sent for catalyst recovery.

And further, in some cases it may be desirable to produce additional electric power and steam from the char by-product.

SUMMARY OF THE INVENTION

The optimum carbon conversion for a catalytic gasification process is generally restricted to be less than 100% to enable the rate of the simultaneous gasification, shift and methanation reactions to be at their maximum values. Typically, the organic carbon content of the bed is maintained at a value that restricts the carbon conversion to 85%-95%. The high efficiency of catalytic gasification to produce substitute natural gas relative to noncatalytic gasification can be achieved despite the lower carbon conversion.

The present invention discloses alternative embodiments to utilize the carbon that is deliberately left unconverted in the hydromethanation reactor during a catalytic gasification process. The unused carbon in the hydromethanation reactor represents a source of energy, either directly as heat or indirectly as synthesis gas, that can potentially further increase the efficiency of the process and improve the economics. In general, the unconverted char may be directly reacted with air or oxygen and steam in an oxidation reactor to produce either a synthesis gas ($H_2$, CO, $CO_2$) with little or no $CH_4$ or a combustion product ($CO_2$, $H_2O$) that can be utilized to produce additional steam and electric power. The process in accordance with the present invention may be useful because it improves carbon utilization in the process, improves the overall thermal efficiency, creates steam and electric power, and reduces the volume of char material processed in catalyst recovery (which allows the use of reduced equipment size), thereby lowering both operating and capital costs of the operation.

In particular, the present invention provides a process for generating, from a non-gaseous carbonaceous material and a hydromethanation catalyst, (1) a fines-cleaned methane-enriched raw product gas stream, (2) an oxidation reactor product gas and (3) an oxidation reactor ash product stream, the process comprising the steps of:

a) preparing a carbonaceous feedstock from the non-gaseous carbonaceous material;

b) introducing the carbonaceous feedstock, the hydromethanation catalyst, steam and oxygen into a hydromethanation reactor, the hydromethanation reactor comprising a fluidized bed, a disengagement zone above the fluidized bed, and a gas mixing zone below the fluidized bed;

c) reacting the carbonaceous feedstock in the hydromethanation reactor in the presence of carbon monoxide, hydrogen, steam and hydromethanation catalyst, and at an operating temperature from about 400° F. (about 205° C.) up to about 1500° F. (about 816° C.), and an operating pressure of at least about 250 psig (about 1825 kPa), to produce a methane-enriched raw product gas, heat energy and a by-product char;

d) withdrawing a stream of methane-enriched raw product gas from the hydromethanation reactor as the methane-enriched raw product gas stream, wherein the methane-enriched raw product gas stream comprises methane, carbon monoxide, hydrogen, carbon dioxide, hydrogen sulfide, steam, and entrained solids;

e) removing a substantial portion of the entrained solids from the methane-enriched raw product gas stream to generate a solids-depleted, methane-enriched raw product gas stream and a recovered primary solids stream;

f) removing a substantial portion of any fines from the solids-depleted, methane-enriched raw product gas stream to generate the fines-cleaned methane-enriched raw product gas stream and a recovered secondary fines stream;

g) withdrawing a stream of by-product char from the hydromethanation reactor as the hydromethanation reactor char product stream, wherein the hydromethanation reactor char product stream comprises a carbon content and entrained hydromethanation catalyst;

h) extracting a portion of the entrained catalyst from the hydromethanation reactor char product stream by the steps of:

(i) feeding all or a portion of the hydromethanation reactor char product stream to a catalyst recovery unit;

(ii) withdrawing a stream of catalyst-depleted char from the catalyst recovery unit as the washed char product stream; and (iii) withdrawing a stream of liberated hydromethanation catalyst from the catalyst recovery unit as the recovered hydromethanation catalyst stream;

i) feeding into an oxidation reactor (1) all or a portion of the washed char product stream, and (2) an oxygen-containing gas stream;

j) reacting at least a portion of the carbon content of the washed char product stream with the oxygen-containing gas stream in the oxidation reactor to produce (1) the oxidation reactor ash product stream, and (2) the oxidation reactor product gas comprising steam and carbon dioxide; and k) withdrawing the oxidation reactor product gas from the oxidation reactor.

In addition, the process may further comprise the steps of: (A) operating the oxidation reactor at a pressure greater than 791 kPa (100 psig); (B) (i) when the oxidation reactor product gas further comprises carbon monoxide and hydrogen, feeding all or a portion of the oxidation reactor product gas into a gas turbine combined cycle system to generate power and steam; or (ii) when carbon monoxide and hydrogen are not present in the oxidation reactor product gas, feeding all or a portion of the oxidation reactor product gas into a gas expander and a heat recovery steam generator to generate power and steam; and (C) cooling or quenching the oxidation reactor ash product stream. In addition, the steps of (D) converting all or a portion of the steam generated in step (B) to power in a steam-turbine generator, and (E) exporting any unused steam are also contemplated.

The process may further comprise the steps of: (A) operating the oxidation reactor at a pressure less than 400 kPa (44 psig); (B) (i) when the oxidation reactor product gas further comprises carbon monoxide and hydrogen, feeding all or a portion of the oxidation reactor product gas to a heat recovery steam generator equipped with an auxiliary burner to generate steam; or (ii) when carbon monoxide and hydrogen are not present in the oxidation reactor product gas, feeding all or a portion of the oxidation reactor product gas to a heat recovery steam generator to generate steam; and (C) cooling or quenching the oxidation reactor ash product stream. The steps of (D) converting all or a portion of the steam generated in step (B) to power in a steam-turbine generator, and (E) exporting any unused steam are also contemplated. The operating pressure in the hydromethanation reactor ranges from at least about 250 psig (about 1825 kPa) up to about 1200 psig (about 8375 kPa). The oxidation reactor may be a fluidized-bed oxidation reactor. The hydromethanation catalyst may comprise an alkali metal, which may be potassium. The hydromethanation catalyst may comprise at least a portion of the recovered hydromethanation catalyst stream.

The process may further comprise the steps of: (f1) feeding the recovered primary solids stream into the hydromethanation reactor; and (f2) feeding all or a portion of the recovered secondary fines stream into the catalyst recovery unit.

The process may further comprise the steps of:

1) introducing the fines-cleaned methane-enriched raw product gas stream into a heat exchanger unit to remove heat energy and generate a cooled methane-enriched raw product stream;

m) steam shifting a portion of the carbon monoxide in the cooled methane-enriched raw product stream in a shift reactor system to generate a hydrogen-enriched raw product gas stream with a molar ratio of hydrogen to carbon monoxide of close to 3;

n) dehydrating the hydrogen-enriched raw product gas stream in a low-temperature gas cooling system, to generate a dry raw gas stream; and o) removing a substantial portion of the carbon dioxide and a substantial portion of the hydrogen sulfide from the dry raw gas stream in an acid gas removal unit to produce a sweetened gas stream comprising a substantial portion of the hydrogen, carbon monoxide and methane from the dry raw gas stream.

The process may further comprise the steps of:

p) reacting the carbon monoxide and hydrogen in the sweetened gas stream in a methanation system in the presence of a methanation catalyst to produce heat energy and a pipeline quality substitute natural gas stream;

q) recovering the heat energy from the catalytic methanation; and r) utilizing at least a portion of the recovered heat energy to generate and superheat a steam stream; and may have a steam demand and a power demand that are met by internal energy integration such that the process requires no net import of steam or power.

BRIEF DESCRIPTION OF THE DRAWINGS

FIG. 2 is a general diagram of an embodiment wherein the oxidation reactor is operated at a high pressure greater than 791 kPa (100 psig) using oxygen or air as the oxidant and steam as a reactant to produce an oxidation gas that is further processed in a gas-turbine combined cycle to produce electric power and steam for export.

FIG. 3 is a general diagram of an alternative embodiment wherein the oxidation reactor uses air as an oxidant and optionally steam as a reactant to produce an oxidation gas that is expanded to produce electric power if at a high pressure and further processed in a heat recovery steam generation system to produce electric power and steam for export.

DEFINITION OF TERMS

Figure 1:
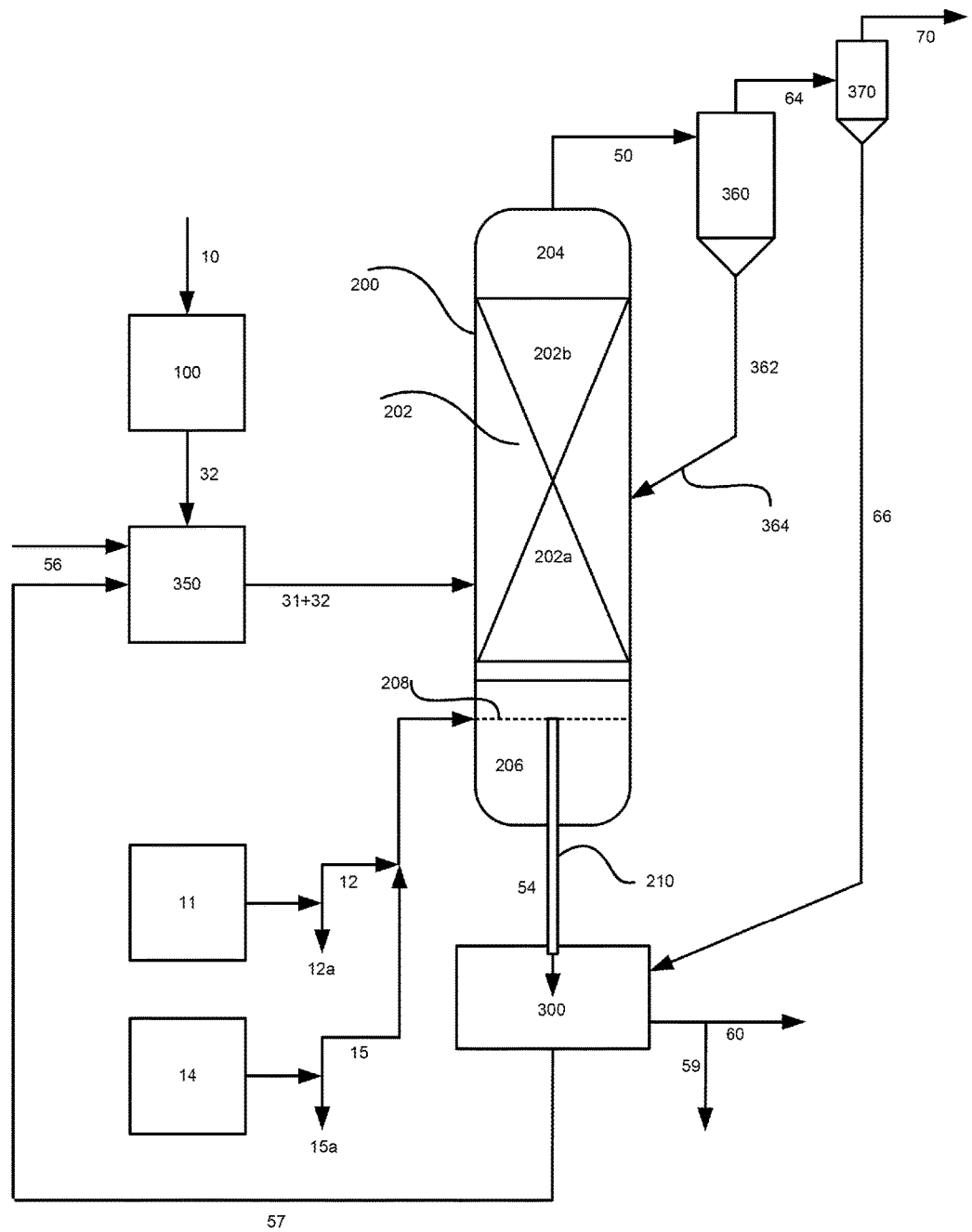
FIG. 1 is a general diagram of the basic hydromethanation process to convert a hydrocarbonaceous feedstock to a fines-cleaned methane-enriched raw product gas stream and a washed char product stream.

The present invention relates to processes for converting a non-gaseous carbonaceous material ultimately into one or more value-added gaseous products.

In the context of the present description, all publications, patent applications, patents and other references mentioned herein, if not otherwise indicated, are explicitly incorporated by reference herein in their entirety for all purposes as if fully set forth.

Unless otherwise defined, all technical and scientific terms used herein have the same meaning as commonly understood by one of ordinary skill in the art to which this disclosure belongs. In case of conflict, the present specification, including definitions, will control.

Except where expressly noted, trademarks are shown in upper case.

Unless stated otherwise, all percentages, parts, ratios, etc., are by weight.

Unless stated otherwise, pressures expressed in psi units are gauge, and pressures expressed in kPa units are absolute. Pressure differences, however, are expressed as absolute (for example, pressure 1 is 25 psi higher than pressure 2).

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

When the term "about" is used in describing a value or an end-point of a range, the disclosure should be understood to include the specific value or end-point referred to.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus.

Further, unless expressly stated to the contrary, "or" and "and/or" refers to an inclusive and not to an exclusive. For example, a condition A or B, or A and/or B, is satisfied by any one of the following: A is true (or present) and B is false (or not present), A is false (or not present) and B is true (or present), and both A and B are true (or present).

The use of "a" or "an" to describe the various elements and components herein is merely for convenience and to give a general sense of the disclosure. This description should be read to include one or at least one, and the singular also includes the plural unless it is obvious that it is meant otherwise.

The term "substantial", as used herein, unless otherwise defined herein, means that greater than about 90% of the referenced material, preferably greater than about 95% of the referenced material, and more preferably greater than about 97% of the referenced material. If not specified, the percent is on a molar basis when reference is made to a molecule (such as methane, carbon dioxide, carbon monoxide and hydrogen sulfide), and otherwise is on a weight basis (such as for entrained solids).

The term "predominant portion", as used herein, unless otherwise defined herein, means that greater than 50% of the referenced material. If not specified, the percent is on a molar basis when reference is made to a molecule (such as hydrogen, methane, carbon dioxide, carbon monoxide and hydrogen sulfide), and otherwise is on a weight basis (such as for entrained solids).

The term "depleted" is synonymous with reduced from originally present. For example, removing a substantial portion of a material from a stream would produce a material-depleted stream that is substantially depleted of that material. Conversely, the term "enriched" is synonymous with greater than originally present.

The term "carbonaceous" as used herein is synonymous with hydrocarbon.

The term "carbonaceous material" as used herein is a material containing organic hydrocarbon content. Carbonaceous materials can be classified as biomass or non-biomass materials as defined herein.

The term "biomass" as used herein refers to carbonaceous materials derived from recently (for example, within the past 100 years) living organisms, including plant-based biomass and animal-based biomass. For clarification, biomass does not include fossil-based carbonaceous materials, such as coal. For example, see previously incorporated US2009/0217575A1, US2009/0229182A1 and US2009/0217587A1.

The term "plant-based biomass" as used herein means materials derived from green plants, crops, algae, and trees, such as, but not limited to, sweet sorghum, bagasse, sugarcane, bamboo, hybrid poplar, hybrid willow, *albizia* trees, *eucalyptus*, alfalfa, clover, oil palm, switchgrass, sudangrass, millet, jatropha, and *miscanthus* (e.g., *Miscanthus* x *giganteus*). Biomass further include wastes from agricultural cultivation, processing, and/or degradation such as corn cobs and husks, corn stover, straw, nut shells, vegetable oils, canola oil, rapeseed oil, biodiesels, tree bark, wood chips, sawdust, and yard wastes.

The term "animal-based biomass" as used herein means wastes generated from animal cultivation and/or utilization. For example, biomass includes, but is not limited to, wastes from livestock cultivation and processing such as animal manure, guano, poultry litter, animal fats, and municipal solid wastes (e.g., sewage).

The term "non-biomass", as used herein, means those carbonaceous materials which are not encompassed by the term "biomass" as defined herein. For example, non-biomass include, but are not limited to, anthracite, bituminous coal, sub-bituminous coal, lignite, petroleum coke, asphaltenes, liquid petroleum residues or mixtures thereof. For example, see US2009/0166588A1, US2009/0165379A1, US2009/0165380A1, US2009/0165361A1, US2009/0217590A1 and US2009/0217586A1.

"Liquid heavy hydrocarbon materials" are viscous liquid or semi-solid materials that are flowable at ambient conditions or can be made flowable at elevated temperature conditions. These materials are typically the residue from the processing of hydrocarbon materials such as crude oil. For example, the first step in the refining of crude oil is normally a distillation to separate the complex mixture of hydrocarbons into fractions of differing volatility. A typical first-step distillation requires heating at atmospheric pressure to vaporize as much of the hydrocarbon content as possible without exceeding an actual temperature of about 650° F., since higher temperatures may lead to thermal decomposition. The fraction which is not distilled at atmospheric pressure is commonly referred to as "atmospheric petroleum residue". The fraction may be further distilled under vacuum, such that an actual temperature of up to about 650° F. can vaporize even more material. The remaining undistillable liquid is referred to as "vacuum petroleum residue". Both atmospheric petroleum residue and vacuum petroleum residue are considered liquid heavy hydrocarbon materials for the purposes of the present process.

Non-limiting examples of liquid heavy hydrocarbon materials include vacuum resids; atmospheric resids; heavy and reduced petroleum crude oils; pitch, asphalt and bitumen (naturally occurring as well as resulting from petroleum refining processes); tar sand oil; shale oil; bottoms from catalytic cracking processes; coal liquefaction bottoms; and other hydrocarbon feedstreams containing significant amounts of heavy or viscous materials such as petroleum wax fractions.

The term "asphaltene" as used herein is an aromatic carbonaceous solid at room temperature, and can be derived, for example, from the processing of crude oil and crude oil tar sands. Asphaltenes may also be considered liquid heavy hydrocarbon feedstocks.

The liquid heavy hydrocarbon materials may inherently contain minor amounts of solid carbonaceous materials, such as petroleum coke and/or solid asphaltenes, that are generally dispersed within the liquid heavy hydrocarbon matrix, and that remain solid at the elevated temperature conditions utilized as the feed conditions for the present process.

The terms "petroleum coke" and "petcoke" as used herein include both (i) the solid thermal decomposition product of high-boiling hydrocarbon fractions obtained in petroleum processing (heavy residues—"resid petcoke"); and (ii) the solid thermal decomposition product of processing tar sands (bituminous sands or oil sands—"tar sands petcoke"). Such carbonization products include, for example, green, calcined, needle and fluidized bed petcoke.

Resid petcoke can also be derived from a crude oil, for example, by coking processes used for upgrading heavy-gravity residual crude oil (such as a liquid petroleum residue), which petcoke contains ash as a minor component, typically about 1.0 wt % or less, and more typically about 0.5 wt % of less, based on the weight of the coke. Typically, the ash in such lower-ash cokes predominantly comprises metals such as nickel and vanadium.

Tar sands petcoke can be derived from an oil sand, for example, by coking processes used for upgrading oil sand. Tar sands petcoke contains ash as a minor component, typically in the range of about 2 wt % to about 12 wt %, and more typically in the range of about 4 wt % to about 12 wt %, based on the overall weight of the tar sands petcoke. Typically, the ash in such higher-ash cokes predominantly comprises materials such as silica and/or alumina.

Petroleum coke can comprise at least about 70 wt % carbon, at least about 80 wt % carbon, or at least about 90 wt % carbon, based on the total weight of the petroleum coke. Typically, the petroleum coke comprises less than about 20 wt % inorganic compounds, based on the weight of the petroleum coke.

The term "coal" as used herein means peat, lignite, sub-bituminous coal, bituminous coal, anthracite, or mixtures thereof. In certain embodiments, the coal has a carbon content of less than about 85%, or less than about 80%, or less than about 75%, or less than about 70%, or less than about 65%, or less than about 60%, or less than about 55%, or less than about 50% by weight, based on the total coal weight. In other embodiments, the coal has a carbon content ranging up to about 85%, or up to about 80%, or up to about 75% by weight, based on the total coal weight. Examples of useful coal include, but are not limited to, Illinois #6, Pittsburgh #8, Beulah (ND), Utah Blind Canyon, and Powder River Basin (PRB) coals. Anthracite, bituminous coal, sub-bituminous coal, and lignite coal may contain about 10 wt %, from about 5 to about 7 wt %, from about 4 to about 8 wt %, and from about 9 to about 11 wt %, ash by total weight of the coal on a dry basis, respectively. However, the ash content of any particular coal source will depend on the rank and source of the coal, as is familiar to those skilled in the art. See, for example, "Coal Data: A Reference", Energy Information Administration, Office of Coal, Nuclear, Electric and Alternate Fuels, U.S. Department of Energy, DOE/EIA-0064(93), February 1995.

The ash produced from combustion of a coal typically comprises both a fly ash and a bottom ash, as is familiar to those skilled in the art. The fly ash from a bituminous coal can comprise from about 20 to about 60 wt % silica and from about 5 to about 35 wt % alumina, based on the total weight of the fly ash. The fly ash from a sub-bituminous coal can comprise from about 40 to about 60 wt % silica and from about 20 to about 30 wt % alumina, based on the total weight of the fly ash. The fly ash from a lignite coal can comprise from about 15 to about 45 wt % silica and from about 20 to about 25 wt % alumina, based on the total weight of the fly ash. See, for example, Meyers, et al. "Fly Ash. A Highway Construction Material," Federal Highway Administration, Report No. FHWA-IP-76-16, Washington, D.C., 1976.

The bottom ash from a bituminous coal can comprise from about 40 to about 60 wt % silica and from about 20 to about 30 wt % alumina, based on the total weight of the bottom ash. The bottom ash from a sub-bituminous coal can comprise from about 40 to about 50 wt % silica and from about 15 to about 25 wt % alumina, based on the total weight of the bottom ash. The bottom ash from a lignite coal can comprise from about 30 to about 80 wt % silica and from about 10 to about 20 wt % alumina, based on the total weight of the bottom ash. See, for example, Moulton, Lyle K. "Bottom Ash and Boiler Slag," Proceedings of the Third International Ash Utilization Symposium, U.S. Bureau of Mines, Information Circular No. 8640, Washington, D.C., 1973.

A material such as methane can be biomass or non-biomass under the above definitions depending on its source of origin.

A "non-gaseous" material is substantially a liquid, semi-solid, solid or mixture at ambient conditions. For example, coal, petcoke, asphaltene and liquid petroleum residue are non-gaseous materials, while methane and natural gas are gaseous materials.

The term "unit" refers to a unit operation. When more than one "unit" is described as being present, those units are operated in a parallel fashion unless otherwise stated. A single "unit", however, may comprise more than one of the units in series, or in parallel, depending on the context. For example, an acid gas removal unit may comprise a hydrogen sulfide removal unit followed in series by a carbon dioxide removal unit. As another example, a contaminant removal unit may comprise a first removal unit for a first contaminant followed in series by a second removal unit for a second contaminant. As yet another example, a compressor may comprise a first compressor to compress a stream to a first pressure, followed in series by a second compressor to further compress the stream to a second (higher) pressure.

The term "a portion of the carbonaceous feedstock" refers to carbon content of unreacted feedstock as well as partially reacted feedstock, as well as other components that may be derived in whole or part from the carbonaceous feedstock (such as carbon monoxide, hydrogen and methane). For example, "a portion of the carbonaceous feedstock" includes carbon content that may be present in by-product char and recycled fines, which char is ultimately derived from the original carbonaceous feedstock.

The term "char" is the combustible residue remaining after the destructive distillation or partial gasification or partial oxidation of coal, petcoke or any other carbonaceous material. Besides the combustible residue, char will contain any mineral matter in the carbonaceous material, including non-volatile portions of catalyst.

"Catalyst-depleted char" is a char material which has undergone a catalyst removal process to recover and reuse soluble catalyst components.

"Carbon-depleted char" is char which has undergone a secondary processing step such as oxidation or gasification or both to convert the carbon residue to gaseous compounds.

The term "entrained catalyst" as used herein means chemical compounds comprising the catalytically active portion of the hydromethanation catalyst, e.g., alkali metal compounds present in the char by-product. For example, "entrained catalyst" can include, but is not limited to, soluble alkali metal compounds (such as alkali metal carbonates, alkali metal hydroxides and alkali metal oxides) and/or insoluble alkali compounds (such as alkali metal aluminosilicates). The nature of catalyst components associated with the char extracted are discussed, for example, in previously incorporated US2007/0277437A1, US2009/0165383A1, US2009/0165382A1, US2009/0169449A1 and US2009/0169448A1.

The term "superheated steam" refers to a steam stream that is non-condensing under the conditions utilized, as is commonly understood by persons of ordinary skill in the relevant art.

The term "steam demand" refers to the amount of steam that must be added to the hydromethanation reactor via the gas feed streams to the hydromethanation reactor. Steam is consumed in the hydromethanation reaction and some steam must be added to the hydromethanation reactor. The theoretical consumption of steam is two moles for every two moles of carbon in the feed to produce one mole of methane and one mole of carbon dioxide (see equation (V)). In actual practice, the steam consumption is not perfectly efficient and steam is withdrawn with the product gases; therefore, a greater than theoretical amount of steam needs to be added to the hydromethanation reactor, which added amount is the "steam demand". Steam can be added, for example, via the steam stream (12) and the oxygen stream (15), which are typically combined prior to introduction into the hydromethanation reactor. The amount of steam to be added (and the source) is discussed in further detail below. Steam generated in situ from the carbonaceous feedstock (e.g., from vaporization of any moisture content of the carbonaceous feedstock, or from an oxidation reaction with hydrogen, methane and/or other hydrocarbons present in or generated from the carbonaceous feedstock) can assist in providing steam; however, it should be noted that any steam generated in situ or fed into the hydromethanation reactor at a temperature lower than the operating temperature within the hydromethanation reactor (the hydromethanation reaction temperature) will have an impact on the "heat demand" for the hydromethanation reaction.

The term "heat demand" refers to the amount of heat energy that must be added to the hydromethanation reactor (for example, via steam stream (12) and/or generated in situ (for example, via a combustion/oxidation reaction with supplied oxygen stream (15) as discussed below) to keep the reaction of carbonaceous feedstock in the hydromethanation reactor in substantial thermal balance, as further detailed below.

The term "power demand" refers to the amount of power that must be used to operate the processes.

The term "substitute natural gas" or "SNG" refers to a methane-rich product gas, typically with a higher heating value greater than 950 BTU/scf, that meets all the specifications for natural gas prescribed by natural gas merchants or pipeline carriers or operators.

Although methods and materials similar or equivalent to those described herein can be used in the practice or testing of the present disclosure, suitable methods and materials are described herein. The materials, methods, and examples herein are thus illustrative only and, except as specifically stated, are not intended to be limiting.

DETAILED INVENTION DESCRIPTION

Basic Process

The basic hydromethanation reactor (HMR) process is shown in FIG. 1. Referring to FIG. 1, the non-gaseous carbonaceous material (10) is processed in a feedstock preparation unit (100) to generate a carbonaceous feedstock (32) which is fed to a catalyst application unit (350) where hydromethanation catalyst (31) is applied to generate a catalyzed carbonaceous feedstock (31+32). The application methods can include mechanical mixing devices to disperse the catalyst solution over the solid feed particles and thermal dryers to achieve the preferred moisture content for the catalyzed carbonaceous feedstocks (31+32).

The feedstock preparation unit (100) includes coal or coke pulverization machines to achieve a pre-determined optimal size distribution which largely depends on the carbonaceous mechanical and chemical properties. In some cases, pelletization and/or briquetting machines are included to consolidate fines to maximize the utilization of all solid feedstock materials. Further details are provided below.

The hydromethanation catalyst (31) will typically comprise a recovered hydromethanation catalyst stream (57) recovered from hydromethanation reactor char product stream (54) and recovered secondary fines (66), and a make-up catalyst from a make-up catalyst stream (56). Further details are provided below.

The catalyzed carbonaceous feedstock (31+32) is fed into a hydromethanation reactor (200) along with steam stream (12) and oxygen stream (15). The location at which the catalyzed carbonaceous feedstock (31+32) is fed may vary. For example, it may be fed into fluidized bed (202) in lower portion (202a), just above the hydromethanation reactor fluidizing gas distributor plate (208), or into the bottom of upper portion (202b).

Steam streams (12) and (12a) are provided by a steam source such as steam distribution system (11), which desirably utilizes process heat recovery (e.g., heat energy recovery from the hot raw product gas and other process sources) such that the process is steam integrated and steam sufficient. Oxygen stream (15) and second oxygen stream (15a), which splits off from oxygen stream (15), is supplied by an air separation unit (14).

The steam stream (12) and oxygen stream (15) may be a single feed stream which comprises, or multiple feed streams which comprise, in combination with the in situ generation of heat energy and syngas, steam and heat energy, as required to at least substantially satisfy, or at least satisfy, steam and heat demands of the hydromethanation reaction that takes place in hydromethanation reactor (200).

In the hydromethanation reactor (200), (i) a portion of the carbonaceous feedstock, steam, hydrogen and carbon monoxide react in the presence of the hydromethanation catalyst to generate a methane-enriched raw product gas (the hydromethanation reaction), and (ii) a portion of the carbonaceous feedstock reacts in the presence of steam and oxygen to generate heat energy and typically carbon monoxide, hydrogen and carbon dioxide (combustion/oxidation reaction). The generated methane-enriched raw product gas is withdrawn from the hydromethanation reactor (200) as a methane-enriched raw product gas stream (50). The withdrawn methane-enriched raw product gas stream (50) typically comprises at least methane, carbon monoxide, carbon dioxide, hydrogen, hydrogen sulfide, steam, and entrained solids.

The hydromethanation reactor (200) comprises a fluidized bed (202) having an upper portion (202b) above a lower portion (202a) and a disengagement zone (204) above the fluidized bed. Hydromethanation reactor (200) also typically comprises a gas mixing zone (206) below the fluidized-bed (202), with the two sections typically being separated by a hydromethanation reactor fluidizing gas distributor plate (208) or similar divider (for example, an array of sparger pipes). Oxygen (15) is mixed with the high-pressure, superheated steam (12), and the mixture introduced into the gas mixing zone (206), into the lower portion (202a) of the fluidized bed (202) via the gas mixing zone (206), into the fluidized bed (202) at other locations, or into a combination thereof, via the hydromethanation reactor fluidizing gas distributor plate (208) or similar divider. Desirably, oxygen is fed into the lower portion of the fluidized bed. Without being bound by any theory, the hydromethanation reaction predominates in upper portion (202b), and an oxidation reaction with oxygen predominates in lower portion (202a). It is believed that there is no specific defined boundary between the two portions, but rather there is a transition as oxygen is consumed (and heat energy and syngas are generated) in lower portion (202a). It is also believed that oxygen consumption is rapid under the conditions present in hydromethanation reactor (200).

At least a portion of the carbonaceous feedstock in lower portion (202a) of fluidized bed (202) will react with oxygen from oxygen stream (15) to generate heat energy, and hydrogen and carbon monoxide (syngas). This includes the reaction of solid carbon from unreacted (fresh) feedstock, partially reacted feedstock (such as char and recycled fines), as well as gases (carbon monoxide, hydrogen, methane and higher hydrocarbons) that may be generated from or carried with the feedstock and recycle fines in lower portion (202a). Generally, some water (steam) may be produced, as well as other by-products such as carbon dioxide depending on the extent of combustion/oxidation and the water gas shift reaction. As indicated above, in hydromethanation reactor (200) (predominantly in upper portion (202b) of fluidized bed (202)) the carbonaceous feedstock, steam, hydrogen and carbon monoxide react in the presence of the hydromethanation catalyst to generate a methane-enriched raw product, which is ultimately withdrawn as a methane-enriched raw product gas stream (50) from the hydromethanation reactor (200).

The reactions of the carbonaceous feedstock in fluidized bed (202) also result in a by-product char comprising unreacted carbon as well as non-carbon content from the carbonaceous feedstock (including hydromethanation catalyst) as described in further detail below. To prevent buildup of the residue in the hydromethanation reactor (200), a solid purge of hydromethanation reactor char product stream (54) is routinely withdrawn (periodically or continuously) via a char withdrawal line (210). The char product stream (54) comprises a carbon content and entrained hydromethanation catalyst.

Char may also be withdrawn from the hydromethanation reactor at other locations such as from the top of fluidized bed (202), at any place within upper portion (202b) and/or lower portion (202a) of fluidized bed (202), and/or at or just below hydromethanation reactor fluidizing gas distributor plate (208). For example, in one embodiment as disclosed in previously incorporated US2012/0102836A1, carbonaceous feedstock (32) (or catalyzed carbonaceous feedstock (31+32)) is fed into lower portion (202a) of fluidized bed (202). Because catalyzed carbonaceous feedstock (31+32) is introduced into lower portion (202a) of fluidized bed (202), at least one char withdrawal line (210) will typically be located at a point such that by-product char is withdrawn from fluidized bed (202) at one or more points above the feed location of catalyzed carbonaceous feedstock (31+32), typically from upper portion (202b) of fluidized bed (202).

Particles too large to be fluidized in fluidized-bed section (202), for example, large-particle by-product char and non-fluidizable agglomerates, are generally collected in lower portion (202a) of fluidized bed (202), as well as in gas mixing zone (206). Such particles will typically comprise a carbon content (as well as an ash and catalyst content) and may be removed periodically from hydromethanation reactor (200) via a char withdrawal line (210) for catalyst recovery and further processing.

All or a portion of hydromethanation reactor char product stream (54) (typically all of such stream) is processed in a catalyst recovery unit (300) to recover entrained hydromethanation catalyst, and optionally other value-added by-products such as vanadium and nickel (depending on the content of the non-gaseous carbonaceous material (10)), to generate a washed char product stream (60) and a recovered hydromethanation catalyst stream (57).

All or a portion of washed char product stream (60) is processed as described below. The remainder of the washed char, (59), may be processed in a boiler to generate steam and power.

In hydromethanation reactor (200), the methane-enriched raw product gas typically passes through the disengagement zone (204) above the fluidized-bed section (202) prior to withdrawal from hydromethanation reactor (200). The disengagement zone (204) may optionally contain, for example, one or more internal cyclones and/or other entrained particle disengagement mechanisms (not shown). The withdrawn methane-enriched raw product gas stream (50) typically comprises at least methane, carbon monoxide, carbon dioxide, hydrogen, hydrogen sulfide, steam, and entrained solids.

The methane-enriched raw product gas stream (50) is initially treated to remove a substantial portion of the entrained solids, typically via a cyclone assembly (for example, one or more internal and/or external cyclones), which may be followed if necessary by optional additional treatments such as venturi scrubbers. In the embodiment as shown in FIG. 1, the cyclone assembly comprises an external primary cyclone (360) followed by an external secondary cyclone (370), but other arrangements would be suitable as well. For example, the cyclone assembly could comprise an internal primary cyclone followed by an external secondary cyclone.

The withdrawn methane-enriched raw product gas stream (50), therefore, is to be considered the raw product prior to fines separation, regardless of whether the fines separation takes place internal to and/or external of hydromethanation reactor (200).

As specifically depicted in FIG. 1, the methane-enriched raw product gas stream (50) is passed from hydromethanation reactor (200) to an external primary cyclone (360) for separation of the predominant portion of entrained solids. While primary cyclone (360) is shown as a single external cyclone for simplicity, as indicated above cyclone assembly (360) may be an internal and/or external cyclone and may also be a series of multiple internal and/or external cyclones.

As shown in FIG. 1, the methane-enriched raw product gas stream (50) is treated in primary cyclone (360) to generate a solids-depleted methane-enriched raw product gas stream (64) and a recovered primary solids stream (362).

Recovered primary solids stream (362) is fed back into hydromethanation reactor (200), for example, into one or more portions of fluidized bed (202) via fines recycle line (364). For example, as disclosed in previously incorporated US2012/0060417A1, recovered fines are fed back into lower portion (202*a*) of fluidized bed (202) via fines recycle line (364).

The solids-depleted methane-enriched raw product gas stream (64) typically comprises at least methane, carbon monoxide, carbon dioxide, hydrogen, hydrogen sulfide, steam, and ammonia, as well as small amounts of contaminants such as remaining residual entrained fines, and other volatilized and/or carried material that may be present in the carbonaceous feedstock. There are typically virtually no (total typically less than about 50 ppm) condensable (at ambient conditions) hydrocarbons present in solids-depleted methane-enriched raw product gas stream (64).

Typically, as shown in FIG. 1, the solids-depleted methane-enriched raw product gas stream (64) will be fed to a secondary cyclone (370) to remove a substantial portion of any remaining fines, generating a fines-cleaned methane-enriched raw product gas stream (70) and a recovered secondary fines stream (66). Recovered secondary fines stream (66) will typically be recycled back to catalyst recovery unit (300).

All or a portion of a recovered secondary fines stream (66) may be co-processed with the withdrawn hydromethanation reactor char product stream (54) in the catalyst recovery unit (300).

The catalyst recovery unit (300) recovers the water-soluble catalyst by conventional solids leaching or washing technologies, extracting a portion of the entrained catalyst to generate a washed product char stream (60) and a recovered hydromethanation catalyst stream (57). Unit (300) may include countercurrent mixer settlers or filter presses with wash zones or any combination of similar solid washing/leaching and dewatering devices. In particular, the catalyst recovery unit (300) may comprise a quench tank and a quench medium, the treatment comprising the steps of: quenching the hydromethanation reactor char product stream (54) with the quench medium to extract a portion of the entrained catalyst to generate a catalyst-depleted char and liberated hydromethanation catalyst; withdrawing a stream of catalyst-depleted char from the catalyst recovery unit (300) as the washed char product stream (60); and withdrawing a stream of liberated hydromethanation catalyst from the catalyst recovery unit (300) as the recovered hydromethanation catalyst stream (57).

The hydromethanation catalyst (31) will typically comprise at least a portion of the recovered hydromethanation catalyst stream (57) and a make-up catalyst from a make-up catalyst stream (56).

The fines-cleaned methane-enriched raw product gas stream (70) can be treated in one or more downstream processing steps to recover heat energy, decontaminate and convert, to one or more value-added products such as, for example, substitute natural gas (pipeline quality), hydrogen, carbon monoxide, syngas, ammonia, methanol and other syngas-derived products, electrical power and steam.

EMBODIMENTS OF THE INVENTION

Figure 2:
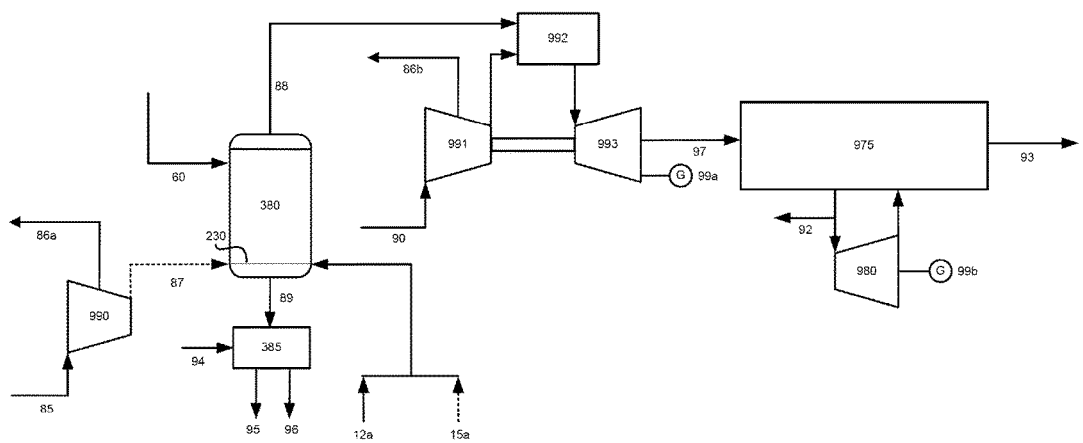
FIGS. 2 and 3 are general diagrams of processes for converting the washed char product stream generated by the basic hydromethanation process to an oxidation reactor product gas in an oxidation reactor and utilizing the oxidation reactor product gas to make steam and electric power, thereby maximizing the overall carbon conversion and overall thermal efficiency.
Figure 3:
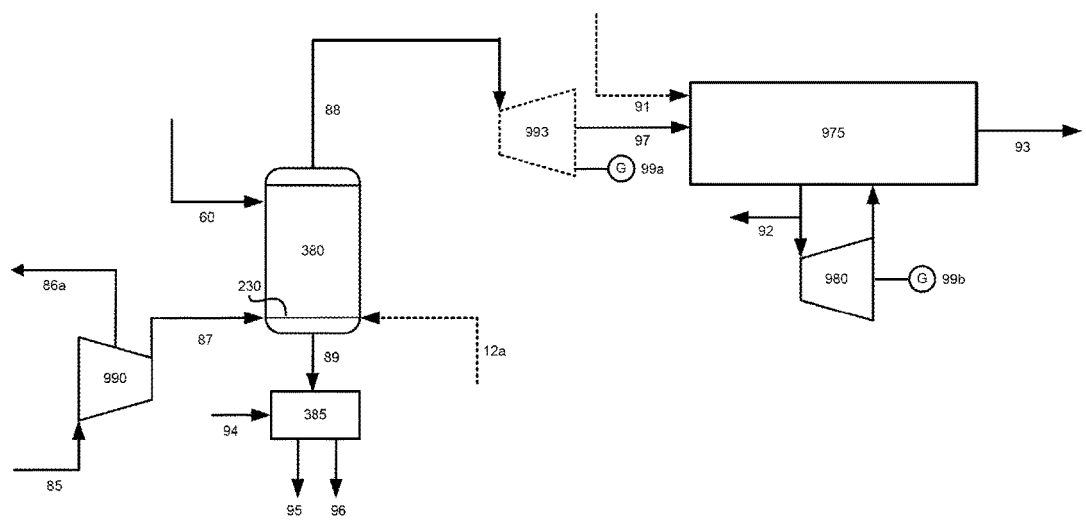

FIGS. 2 and 3 represent two of the alternative embodiments of the catalytic gasification process that aim to maximize the overall carbon conversion and power generated from the process.

The washed char stream (60) is further processed in the oxidation reactor (380) with either oxygen or air to convert the residual carbon present in the washed char stream (60). The alternative embodiments differ in three ways: (1) the pressure of operation of the oxidation reactor (380), (2) the type of oxidant chosen to convert the carbon, and (3) the molecular ratio of gaseous oxygen to carbon in the feed streams to the oxidation reactor (380).

The oxidant is an oxygen-containing gas stream, comprising compressed air (87) or oxygen (15*a*) from air separation unit (14), and, optionally, diluent steam (12*a*). The pressure of the oxidant is greater than the operating pressure of the oxidation reactor (380).

The composition of the oxidation reactor product gas (88) depends on the molecular ratio of oxygen to carbon in the streams entering oxidation reactor (380). When the molecular ratio of oxygen to carbon is controlled to be less than 0.5 and a sufficient quantity of steam is also fed to the oxidation reactor (380), the gas (88) is a syngas comprised of hydrogen, carbon monoxide, carbon dioxide, nitrogen and unreacted steam. The mode of operation is known as the partial oxidation mode wherein oxygen is completely consumed within the oxidation reactor (380). On the other hand, when the molecular ratio of oxygen to carbon is controlled to be greater than one (combustion-mode), the gas (88) is a flue gas comprised of carbon dioxide, steam, nitrogen and unreacted oxygen.

First Embodiment of the Invention

FIG. 2 illustrates one of the embodiments of the process for converting a non-gaseous carbonaceous material ultimately into one or more value-added gaseous products where the oxidation reactor is operated at a pressure greater than 791 kPa (100 psig) in syngas-mode. In accordance with this embodiment, the washed char stream (60) produced by the basic hydromethanation process described above and in FIG. 1 is further processed in an oxidation reactor (380) with steam (12*a*) and either oxygen (15*a*) or compressed air (87) as the oxidant. Air compressor or blower (990) produces compressed air (87) and, optionally, stream (86*a*), from air (85). The process yields an oxidation reactor ash product stream (89) and an oxidation reactor product gas (88). The oxidation gas is then utilized to produce electric power and steam as described below.

The oxidation reactor ash product stream (89) exiting the oxidation reactor is cooled by a coolant stream (94) to produce a cooled product ash (95) and a warmed coolant stream (96). The ash cooler (385) can be any number of direct or indirect heat transfer devices, such as an air-blown fluidized bed, a fluidized bed with steam or water cooling coils, a direct water quench vessel or a water cooled mechanical screw.

Since the oxidation reactor (380) is operated at high pressure in this embodiment, it is advantageous to recover and convert the potential energy of the pressurized oxidation gases to mechanical work and electric power. The oxidation reactor product gas (88) produced is rich in hydrogen and carbon monoxide and is burned directly in a high-pressure gas turbine combustion chamber (992).

Prior to combustion, gas (88) may be processed to remove particulate matter entrained from the oxidation reactor. Suitable mechanisms for removing particulates from the hot oxidation gas include stage cyclones, candle filters and other similar devices (not shown).

Gas (88) is then reacted with atmospheric air (90) compressed to match the pressure of the combustion chamber (992). The air compressor (991) is typically coupled to a gas expander (993). The work recovered by the gas expander (993) drives both the air compressor (991) and an electric generator "G" (99a).

The expander exhaust gas (97) is directed to a heat recovery steam generator (975). The heat recovery steam generator (975) consists of several coils to preheat boiler feed water and produce steam, some of which may be extracted for process use and the balance exported as steam (92). The balance of the steam is directed to a steam turbine (980) to recover additional work and generate more electricity by the electric generator "G" (99b), which is coupled to the steam turbine. The steam turbine can be either back pressure or condensing, with multiple stages and extraction ports if needed. A condensing turbine will maximize the electric power generated by the steam turbine. The heat recovery steam generator (975) also produces flue gas (93).

Second Embodiment of the Invention

FIG. 3 illustrates a second preferred embodiment of the process for converting a non-gaseous carbonaceous material ultimately into one or more value-added gaseous products. The oxidant used is compressed air (87) produced by air compressor or blower (990) from air (85); stream (86a) is also produced. The oxidation reactor (380) may be operated at a high pressure greater than 791 kPa (100 psig) or at a low pressure less than 400 kPa (44 psig). The ratio of air flow rate to the flow rate of the washed char stream (60) produced by the basic hydromethanation process described above and in FIG. 1 may be controlled to allow operation in the syngas-mode or combustion-mode, as described above. In the syngas-mode, the oxidation reactor (380) may also be supplied with steam (12a) in addition to compressed air (87) to yield an oxidation reactor ash product stream (89) and an oxidation reactor product gas (88). The oxidation reactor ash product stream (89) is cooled in ash cooler (385) by a coolant stream (94) to produce a cooled product ash (95) and a warmed coolant stream (96). The oxidation gas is then utilized to produce electric power and steam as described below.

When the oxidation reactor (380) is operated at high pressure, the potential energy of the pressurized oxidation reactor product gas (88) may be converted to mechanical work and electric power in a gas expander (993). The work recovered by the gas expander (993) in this case drives the electric generator "G" (99a).

When the oxidation reactor (380) is operated in syngas-mode, the heat recovery steam generator (975) will be equipped with an auxiliary burner (not shown) to combust the expander exhaust gas (97) with air (91) to form oxidation products comprised of carbon dioxide and water to allow discharge to the atmosphere as flue gas (93).

The expander exhaust gas (97) is subsequently processed in the heat recovery steam generator (975) and steam turbine (980) to produce steam (92) and power (99b) as described in the first embodiment of the process.

In all cases, the flue gas (93) is treated to remove particulate matter and sulfur oxides using standard air pollution control equipment (not shown).

Unit Operations and Processing Details
Hydromethanation (200)

As illustrated in FIG. 1, catalyzed carbonaceous feedstock (31+32), a steam stream (12), and an oxygen stream (15) are introduced into hydromethanation reactor (200).

Char by-product removal from hydromethanation reactor (200) can be at any desired place or places, for example, at the top of fluidized bed (202), at any place within upper portion (202b) and/or lower portion (202a) of fluidized bed (202), and/or at or just below hydromethanation reactor fluidizing gas distributor plate (208). As indicated above, the location where catalyzed carbonaceous feedstock (31+32) is introduced will have an influence on the location of a char withdrawal point.

Typically, there will be at least one char withdrawal point at or below hydromethanation reactor fluidizing gas distributor plate (208) to withdraw char comprising larger or agglomerated particles.

Hydromethanation reactor (200) is typically operated at moderately high pressures and temperatures, requiring introduction of solid streams (e.g., catalyzed carbonaceous feedstock (31+32) and, if present, recycle fines) to the reaction chamber of the reactor while maintaining the required temperature, pressure and flow rate of the streams. Those skilled in the art are familiar with feed inlets to supply solids into the reaction chambers having high pressure and/or temperature environments, including star feeders, screw feeders, rotary pistons and lock-hoppers. It should be understood that the feed inlets can include two or more pressure-balanced elements, such as lock hoppers, which would be used alternately. In some instances, the carbonaceous feedstock can be prepared at pressure conditions above the operating pressure of the reactor and, hence, the particulate composition can be directly passed into the reactor without further pressurization. Gas for pressurization can be an inert gas such as nitrogen, or more typically a stream of carbon dioxide that can, for example be recycled from a carbon dioxide stream generated by an acid gas removal unit.

Hydromethanation reactor (200) is desirably operated at a moderate temperature (as compared to "conventional" oxidation-based gasification processes), with an operating temperature of from about 400° F. (about 205° C.), or from about 1000° F. (about 538° C.), or from about 1100° F. (about 593° C.), or from about 1200° F. (about 649° C.), to about 1500° F. (about 816° C.), or to about 1400° F. (about 760° C.), or to about 1375° F. (about 746° C.); and a pressure of at least about 250 psig (about 1825 kPa, absolute), or at least about 400 psig (about 2860 kPa), or at least about 450 psig (about 3204 kPa). Typically, the pressure can range up to the levels of mechanical feasibility, for example, up to about 1200 psig (about 8375 kPa), up to about 1000 psig (about 6996 kPa), or to about 800 psig (about 5617 kPa), or to about 700 psig (about 4928 kPa), or to about 600 psig (about 4238 kPa), or to about 500 psig (about 3549 kPa). In one embodiment, hydromethanation reactor (200) is operated at a pressure (first operating pressure) of up to about 600 psig (about 4238 kPa), or up to about 550 psig (about 3894 kPa).

Typical gas flow velocities in hydromethanation reactor (200) are from about 0.5 ft/sec (about 0.15 m/sec), or from about 1 ft/sec (about 0.3 m/sec), to about 2.0 ft/sec (about 0.6 m/sec), or to about 1.5 ft/sec (about 0.45 m/sec).

As oxygen stream (15) is fed into hydromethanation reactor (200), a portion of the carbonaceous feedstock (desirably carbon from the partially reacted feedstock, by-product char and recycled fines) will be consumed in an oxidation/combustion reaction, generating heat energy as well as typically some amounts carbon monoxide and hydrogen (and typically other gases such as carbon dioxide and steam). The variation of the amount of oxygen supplied to hydromethanation reactor (200) provides an advantageous process control to ultimately maintain the syngas and heat balance. Increasing the amount of oxygen will increase the oxidation/combustion, and therefore increase in situ heat generation. Decreasing the amount of oxygen will conversely decrease the in situ heat generation. The amount of syngas generated will ultimately depend on the amount of oxygen utilized, and higher amounts of oxygen may result in a more complete combustion/oxidation to carbon dioxide and water, as opposed to a more partial combustion to carbon monoxide and hydrogen.

The amount of oxygen supplied to hydromethanation reactor (200) must be sufficient to combust/oxidize enough of the carbonaceous feedstock to generate enough heat energy and syngas to meet the heat and syngas demands of the steady-state hydromethanation reaction.

A portion of the oxygen (second oxygen stream 15a) is fed into an oxidation reactor (380) along with a portion of the steam (steam stream 12a) to react with by-product char as discussed in further detail below.

In one embodiment, the total amount of molecular oxygen that is provided to the hydromethanation reactor (200), or the hydromethanation reactor (200) and oxidation reactor (380) combined, can range from about 0.10, or from about 0.20, or from about 0.25, to about 0.6, or to about 0.5, or to about 0.4, or to about 0.35 weight units (for example, pound or kg) of $O_2$ per weight unit (for example, pound or kg) of carbonaceous feedstock (32).

The hydromethanation and oxidation/combustion reactions within hydromethanation reactor (200) will occur contemporaneously. Depending on the configuration of hydromethanation reactor (200), the two steps will typically predominate in separate zones—the hydromethanation in upper portion (202b) of fluidized bed (202), and the oxidation/combustion in lower portion (202a) of fluidized bed (202).

Oxygen stream (15) is typically mixed with steam stream (12) and the mixture introduced at or near the bottom of fluidized bed (202) in lower portion (202a) through hydromethanation reactor fluidizing gas distributor plate (208) to avoid formation of hot spots in the reactor, to avoid (minimize) combustion of the desired gaseous products generated within hydromethanation reactor (200), and to improve the safety of the operation. Feeding the catalyzed carbonaceous feedstock (31+32) with an elevated moisture content, and particularly into lower portion (202a) of fluidized bed (202), also assists in heat dissipation and the avoidance of formation of hot spots in reactor (200), as disclosed in previously incorporated US2012/0102837A1.

Oxygen stream (15) can be fed into hydromethanation reactor (200) by any suitable means such as direct injection of purified oxygen, oxygen-air mixtures, oxygen-steam mixtures, or oxygen-inert gas mixtures into the reactor. See, for instance, U.S. Pat. No. 4,315,753 and Chiaramonte et al., Hydrocarbon Processing, September 1982, pp. 255-257. Oxygen stream (15) and second oxygen stream (15a), which splits off from oxygen stream (15), is supplied by an air separation unit (14).

Oxygen stream (15) is typically generated via standard air-separation technologies, and will be fed mixed with steam, and introduced at a temperature above about 250° F. (about 121° C.), to about 400° F. (about 204° C.), or to about 350° F. (about 177° C.), or to about 300° F. (about 149° C.), and at a pressure at least slightly higher than present in hydromethanation reactor (200). The steam in oxygen stream (15) should be non-condensable during transport of oxygen stream (15) to hydromethanation reactor (200), so oxygen stream (15) may need to be transported at a lower pressure then pressurized (compressed) just prior to introduction into hydromethanation reactor (200).

As indicated above, the hydromethanation reaction has a steam demand, a heat demand and a syngas demand. These conditions in combination are important factors in determining the operating conditions for the hydromethanation reaction as well as the remainder of the process.

For example, the hydromethanation reaction requires a theoretical molar ratio of steam to carbon (in the feedstock) of at least about 1. Typically, however, the molar ratio is greater than about 1, or from about 1.5 (or greater), to about 6 (or less), or to about 5 (or less), or to about 4 (or less), or to about 3 (or less), or to about 2 (or less). The moisture content of the catalyzed carbonaceous feedstock (31+32), moisture generated from the carbonaceous feedstock in the hydromethanation reactor (200), and steam included in the steam stream (12), oxygen stream (15), oxidation reactor product gas stream (88) and recycle fines stream(s) all contribute steam for the hydromethanation reaction. The steam in steam stream (12), oxygen stream (15) and oxidation gas stream (88) should be sufficient to at least substantially satisfy (or at least satisfy) the "steam demand" of the hydromethanation reaction.

As also indicated above, the hydromethanation reaction is essentially thermally balanced but, due to process heat losses and other energy requirements (for example, vaporization of moisture on the feedstock), some heat must be generated in situ (in hydromethanation reactor (200)) to maintain the thermal balance (the heat demand). The partial combustion/oxidation of carbon in the presence of the oxygen introduced into hydromethanation reactor (200) from oxygen stream (15) should be sufficient to at least substantially satisfy (or at least satisfy) both the heat and syngas demand of the hydromethanation reaction.

The gas utilized in hydromethanation reactor (200) for pressurization and reaction of the catalyzed carbonaceous feedstock (31+32) comprises the steam stream (12), oxygen stream (15) and, optionally, additional nitrogen, air, or inert gases such as argon, which can be supplied to hydromethanation reactor (200) according to methods known to those skilled in the art. As a consequence, steam stream (12) and oxygen stream (15) must be provided at a higher pressure which allows them to enter hydromethanation reactor (200).

Steam stream (12) can be at a temperature as low as the saturation point at the feed pressure, but it is desirable to feed at a temperature above this to avoid the possibility of any condensation occurring. Typical feed temperatures of superheated steam stream (12) are from about 500° F. (about 260° C.), or from about 600° F. (about 316° C.), or from about 700° F. (about 371° C.), to about 950° F. (about 510° C.), or to about 900° F. (about 482° C.). Typical feed pressures of steam stream (12) are about 25 psi (about 172 kPa) or greater than the pressure within hydromethanation reactor (200).

The actual temperature and pressure of steam stream (12) will ultimately depend on the level of heat recovery from the process and the operating pressure within hydromethanation reactor (200), as discussed below.

When steam stream (12) and oxygen stream (15) are combined for feeding into lower section (202a) of fluidized bed (202), the temperature of the combined stream will be controlled by the temperature of steam stream (12), and will typically range from about from about from about 400° F. (about 204° C.), or from about 450° F. (about 232° C.), to about 800° F. (about 455° C.), or to about 600° F. (about 316° C.).

The temperature in hydromethanation reactor (200) can be controlled, for example, by controlling the amount and temperature of steam stream (12) as well as the amount of oxygen supplied to hydromethanation reactor (200).

In steady-state operation, steam for hydromethanation reactor (200) and oxidation reactor (380) is desirably solely generated from other process operations through process heat capture (such as generated in a waste heat boiler, generally referred to as "process steam" or "process-generated steam", and referenced as steam source (11)), specifically from the cooling of the raw product gas in a heat exchanger unit. Additional steam can be generated for other portions of the overall process, such as disclosed, for example, in previously incorporated US2010/0287835A1 and US2012/0046510A1, and as shown in FIGS. 2 and 3 discussed below.

The result of the hydromethanation reaction is a methane-enriched raw product, which is withdrawn from hydromethanation reactor (200) as methane-enriched raw product gas stream (50) typically comprising $CH_4$, $CO_2$, $H_2$, CO, $H_2S$, unreacted steam and, optionally, other contaminants such as entrained solids, $NH_3$, COS, HCN and/or elemental mercury vapor, depending on the nature of the carbonaceous material utilized for hydromethanation.

The non-gaseous carbonaceous materials (10) useful in these processes include, for example, a wide variety of biomass and non-biomass materials. The carbonaceous feedstock (32) is derived from one or more non-gaseous carbonaceous materials (10), which are processed in a feedstock preparation unit (100) as discussed below.

The hydromethanation catalyst (31) can comprise one or more catalyst species, as discussed below.

The carbonaceous feedstock (32) and the hydromethanation catalyst (31) are typically intimately mixed (i.e., to provide a catalyzed carbonaceous feedstock (31+32)) before provision to the hydromethanation reactor (200), but they can be fed separately as well.

The hot gas effluent leaving the reaction chamber of the hydromethanation reactor (200) can pass through a fines remover unit (such as cyclone assembly (360)), incorporated into and/or external of the hydromethanation reactor (200), which serves as a disengagement zone. Particles too heavy to be entrained by the gas leaving the hydromethanation reactor (200) (i.e., fines) are returned to the hydromethanation reactor (200), for example, to the reaction chamber (e.g., fluidized bed (202)).

Residual entrained solids are substantially removed by any suitable device such as internal and/or external cyclone separators to generate a solids-depleted methane-enriched raw product gas stream (64). As discussed above, at least a portion of these fines can be returned to fluidized bed (202) via recycle line (364). Any remaining recovered fines can be processed to recover alkali metal catalyst, and/or combined at some stage with carbonaceous feedstock (32), and/or directly recycled back to feedstock preparation as described in previously incorporated US2009/0217589A1.

Removal of a "substantial portion" of fines means that an amount of fines is removed from the resulting gas stream such that downstream processing is not adversely affected; thus, at least a substantial portion of fines should be removed. Some minor level of ultrafine material may remain in the resulting gas stream to the extent that downstream processing is not significantly adversely affected. Typically, at least about 90 wt %, or at least about 95 wt %, or at least about 98 wt %, of the fines of a particle size greater than about 20 μm, or greater than about 10 μm, or greater than about 5 μm, are removed.

Additional residual entrained fines may be removed from the solids-depleted methane-enriched raw product gas stream (64) by any suitable device such as internal and/or external cyclone separators such as external secondary cyclone (370), optionally followed by scrubbers. The resulting fines-cleaned methane-enriched raw product gas stream (70) can be further processed for heat recovery and/or purification/conversion as required to achieve a desired end product, as disclosed in the numerous previously incorporated disclosures set forth above in the "Hydromethanation" section. Reference may be had to those disclosures for further details.

Oxidation Reactor (380)

Oxidation reactor (380) can be any type of oxidation/combustion reactor suitable for reacting the by-product char with oxygen or air and steam under the conditions specified by the embodiments of this invention. Suitable reactors are in a general sense well-known to those of ordinary skill in the relevant art.

Preferably, the oxidation reactor (380) is a fluidized-bed reactor which, in operation, contains a fluidized bed of the by-product char fluidized by steam (12a) and oxygen (15a) or compressed air (87) fed into the reactor through oxidation reactor fluidizing gas distributor plate (230).

The oxidation reactor may include internal and external cyclones (not shown) to remove particles from the oxidation gas. The recovered particles maybe recycled to oxidation reactor as is typical for a fluid bed or the particles may be directed to the char cooling system for disposal.

Oxidation reactor (380) operates at a temperature of about 1800° F. (about 982° C.) or less, or about 1450° F. (about 788° C.) or less, or about 1400° F. (about 760° C.) or less. The pressure of operation of the oxidation reactor (380) may be chosen independent of the hydromethanation reactor (200) since they are decoupled. In the oxidation reactor (380), all or a portion of the carbon content of the by-product char is reacted with steam and oxygen or air to produce a carbon-depleted char and an oxidation gas comprising steam, carbon monoxide, carbon dioxide, hydrogen, and nitrogen (if air is used as an oxidant). A stream of the oxidation gas is withdrawn from oxidation reactor (380) as oxidation reactor product gas stream (88), and a stream of carbon-depleted char is withdrawn from oxidation reactor as oxidation reactor ash product stream (89).

The oxidation reactor product gas stream (88) is a "medium BTU gas" if the constituents are primarily steam, CO, $CO_2$ and $H_2$. Gas stream (88) is a "low BTU gas" if the constituents are primarily nitrogen, CO, $CO_2$, $H_2$ and steam. Gas stream (88) is a "flue gas" with no chemical energy content if the constituents are primarily nitrogen, steam and $CO_2$.

The oxidation reactor product gas (88) is utilized to produce steam and electric power, which are the main objectives of this invention and the details of which are described elsewhere.

Air Compressor (990)

An air compressor or blower (990) compresses air (85), supplying compressed air (87) to the oxidation reactor (380). A number of commercially available machines are available for this application. Compressors are staged to achieve progressively higher pressures. Centrifugal compressors or turboblowers are widely used to handle large volumes of gas from 0.5 up to several hundred psi. For air, the typical pressure ratio per stage is 1.4. The gas is cooled between stages as the work of compression will cause the air to increase in temperature.

Rotary compressors and blowers, screw compressors and reciprocating compressors can also be used for this application. The choice of machine is application dependent;

important selection factors are the required pressure ratio, volume of air and machine costs and efficiency.

When the pressure of the compressed air (87) exceeds the pressure of the air required for the air separation unit (14), all or a portion of the compressed air required for air separation may be extracted as stream (86*a*). Similarly, when the air compressor (991) is operated at a pressure higher than that of the air required for the air separation unit (14), all or a portion of the compressed air required for air separation may be extracted as stream (86*b*).

Ash Cooler (385)

The ash cooler is a device to reduce the temperature and often the pressure of the solid product from the oxidation reactor (380) so the material can be safely handled and disposed. A number of different devices can be employed to achieve this goal. The simplest device is a direct quench system whereby the char or ash is dropped into a pool of cooler water. The water drops the temperature of the char by direct contact and the resultant water/solids slurry can then be depressurized and further cooled if need be. The slurry can be depressurized by expanding through an abrasion resistant control valve or let down through an arrangement of lock hoppers.

Another means of cooling the char or ash is to direct the material into a fluid bed with internal cooling coils. The bed may be fluidized with cold air and the coils may contain cooling fluid such as water. The heat transfer between coils and solids in a fluid bed is known to occur with high efficiency. The main advantage of this method is the char or ash can be withdrawn dry.

A third option is to cool the char by a cooling screw. This device employs a transfer screw encased in a water cooled jacket. The screw may also be internally cooled. Again, the char or ash can be kept dry as it is cooled If the char is at pressure a separate method to depressurize the cooled char may be required, such as lock hoppers or slide valves.

Catalyst Recovery (300)

The hydromethanation reactor char product stream (54) typically comprises inorganic ash and entrained catalyst, as well as residual carbon. This char is passed to a catalyst recovery unit (300).

In certain embodiments, when the hydromethanation catalyst is an alkali metal, the alkali metal in the hydromethanation reactor char product stream (54) can be recovered to produce a recovered hydromethanation catalyst stream (57), and any unrecovered catalyst can be compensated by a make-up catalyst stream (56) (see, for example, previously incorporated US2009/0165384A1). The more alumina plus silica that is in the feedstock, the more costly it is to obtain a higher alkali metal recovery.

Ultimately, the recovered hydromethanation catalyst stream (57) can be directed to the catalyst application unit (350) for reuse of the alkali metal catalyst.

Other particularly useful recovery and recycling processes are described in U.S. Pat. No. 4,459,138, as well as previously incorporated US2007/0277437A1 US2009/0165383A1, US2009/0165382A1, US2009/0169449A1 and US2009/0169448A1. Reference can be had to those documents for further process details.

The recycle of catalyst can be to one or a combination of catalyst loading processes. For example, all of the recycled catalyst can be supplied to one catalyst loading process, while another process utilizes only makeup catalyst. The levels of recycled versus makeup catalyst can also be controlled on an individual basis among catalyst loading processes.

The washed char product stream (60) can also be treated for recovery of other by-products, such as vanadium and/or nickel, in addition to catalyst recovery, as disclosed in previously incorporated US2011/0262323A1 and US2012/0213680A1.

As indicated above, recovered secondary fines stream (66) can be co-treated in catalyst recovery unit (300).

In this embodiment, the washed char stream (60) is further processed so it can be fed into the oxidation reactor (380). These processing steps could include direct thermal drying, pelletization and thermal drying or briquetting.

Preparation of Carbonaceous Feedstocks

Carbonaceous Materials Processing (100)

Particulate carbonaceous materials, such as biomass and non-biomass, can be prepared via crushing and/or grinding, either separately or together, according to any methods known in the art, such as impact crushing and wet or dry grinding to yield one or more carbonaceous particulates. Depending on the method utilized for crushing and/or grinding of the carbonaceous material sources, the resulting carbonaceous particulates may be sized (i.e., separated according to size) to provide the carbonaceous feedstock (32) for use in catalyst application unit (350) to form a catalyzed carbonaceous feedstock (31+32) for the hydromethanation reactor (200).

Any method known to those skilled in the art can be used to size the particulates. For example, sizing can be performed by screening or passing the particulates through a screen or number of screens. Screening equipment can include grizzlies, bar screens, and wire mesh screens. Screens can be static or incorporate mechanisms to shake or vibrate the screen. Alternatively, classification can be used to separate the carbonaceous particulates. Classification equipment can include ore sorters, gas cyclones, hydrocyclones, rake classifiers, rotating trommels or fluidized classifiers. The carbonaceous materials can be also sized or classified prior to grinding and/or crushing.

The carbonaceous particulate can be supplied as a fine particulate having an average particle size of from about 25 microns, or from about 45 microns, up to about 2500 microns, or up to about 500 microns. One skilled in the art can readily determine the appropriate particle size for the carbonaceous particulates. For example, for a fluidized bed reactor, such carbonaceous particulates can have an average particle size which enables incipient fluidization of the carbonaceous materials at the gas velocity used in the fluidized bed reactor. Desirable particle size ranges for the hydromethanation reactor (200) are in the Geldart A and Geldart B ranges (including overlap between the two), depending on fluidization conditions, typically with limited amounts of fine (below about 25 microns) and coarse (greater than about 250 microns) material.

Additionally, certain carbonaceous materials, for example, corn stover and switchgrass, and industrial wastes, such as saw dust, either may not be amenable to crushing or grinding operations, or may not be suitable for use as such, for example due to ultrafine particle sizes. Such materials may be formed into pellets or briquettes of a suitable size for crushing or for direct use in, for example, a fluidized bed reactor. Generally, pellets can be prepared by compaction of one or more carbonaceous material; see for example, previously incorporated US2009/0218424A1. In other examples, a biomass material and a coal can be formed into briquettes as described in U.S. Pat. Nos. 4,249,471, 4,152,119 and 4,225,457. Such pellets or briquettes can be used interchangeably with the preceding carbonaceous particulates in the following discussions.

Additional feedstock processing steps may be necessary depending on the qualities of carbonaceous material sources. Biomass may contain high moisture contents, such as green plants and grasses, and may require drying prior to crushing. Municipal wastes and sewages also may contain high moisture contents which may be reduced, for example, by use of a press or roll mill (e.g., U.S. Pat. No. 4,436,028). Likewise, non-biomass, such as high-moisture coal, can require drying prior to crushing. Some caking coals can require partial oxidation to simplify operation. Non-biomass feedstocks deficient in ion-exchange sites, such as anthracites or petroleum cokes, can be pre-treated to create additional ion-exchange sites to facilitate catalyst loading and/or association. Such pre-treatments can be accomplished by any method known to the art that creates ion-exchange capable sites and/or enhances the porosity of the feedstock (see, for example, previously incorporated U.S. Pat. No. 4,468,231 and GB1599932). Oxidative pre-treatment can be accomplished using any oxidant known to the art.

The ratio and types of the carbonaceous materials in the carbonaceous particulates can be selected based on technical considerations, processing economics, availability, and proximity of the non-biomass and biomass sources. The availability and proximity of the sources for the carbonaceous materials can affect the price of the feeds, and thus the overall production costs of the catalytic gasification process. For example, the biomass and the non-biomass materials can be blended in at about 5:95, about 10:90, about 15:85, about 20:80, about 25:75, about 30:70, about 35:65, about 40:60, about 45:55, about 50:50, about 55:45, about 60:40, about 65:35, about 70:20, about 75:25, about 80:20, about 85:15, about 90:10, or about 95:5 by weight on a wet or dry basis, depending on the processing conditions.

Significantly, the carbonaceous material sources, as well as the ratio of the individual components of the carbonaceous particulates, for example, a biomass particulate and a non-biomass particulate, can be used to control other material characteristics of the carbonaceous particulates. Non-biomass materials, such as coals, and certain biomass materials, such as rice hulls, typically include significant quantities of inorganic matter including calcium, alumina and silica which form inorganic oxides (i.e., ash) in the catalytic gasifier. At temperatures above about 500° C. to about 600° C., potassium and other alkali metals can react with the alumina and silica in ash to form insoluble alkali aluminosilicates. In this form, the alkali metal is substantially water-insoluble and inactive as a catalyst. To prevent buildup of the residue in the hydromethanation reactor (200), as described above a solid purge of hydromethanation reactor char product stream (54) comprising ash, unreacted carbonaceous material, and various other compounds (such as alkali metal compounds, both water soluble and water insoluble) is withdrawn and processed.

In preparing the carbonaceous particulates, the ash content of the various carbonaceous materials can be selected to be, for example, about 20 wt % or less, or about 15 wt % or less, or about 10 wt % or less, or about 5 wt % or less, depending on, for example, the ratio of the various carbonaceous materials and/or the starting ash in the various carbonaceous materials. In other embodiments, the resulting the carbonaceous particulates can comprise an ash content ranging from about 5 wt %, or from about 10 wt %, to about 20 wt %, or to about 15 wt %, based on the weight of the carbonaceous particulate. In other embodiments, the ash content of the carbonaceous particulate can comprise less than about 20 wt %, or less than about 15 wt %, or less than about 10 wt %, or less than about 8 wt %, or less than about 6 wt % alumina, based on the weight of the ash. In certain embodiments, the carbonaceous particulates can comprise an ash content of less than about 20 wt %, based on the weight of processed feedstock where the ash content of the carbonaceous particulate comprises less than about 20 wt % alumina, or less than about 15 wt % alumina, based on the weight of the ash.

Such lower alumina values in the carbonaceous particulates allow for, ultimately, decreased losses of catalysts, and particularly alkali metal catalysts, in the hydromethanation portion of the process. As indicated above, alumina can react with alkali source to yield an insoluble char component comprising, for example, an alkali aluminate or aluminosilicate. Such insoluble char component can lead to decreased catalyst recovery (i.e., increased catalyst loss), and thus, require additional costs of make-up catalyst in the overall process.

Additionally, the resulting carbonaceous particulates can have a significantly higher % carbon, and thus btu/lb value and methane product per unit weight of the carbonaceous particulate. In certain embodiments, the resulting carbonaceous particulates can have a carbon content ranging from about 75 wt %, or from about 80 wt %, or from about 85 wt %, or from about 90 wt %, up to about 95 wt %, based on the combined weight of the non-biomass and biomass.

In one example, a non-biomass and/or biomass is wet ground and sized (e.g., to a particle size distribution of from about 25 to about 2500 μm) and then drained of its free water (i.e., dewatered) to a wet cake consistency. Examples of suitable methods for the wet grinding, sizing, and dewatering are known to those skilled in the art; for example, see previously incorporated US2009/0048476A1. The filter cakes of the non-biomass and/or biomass particulates formed by the wet grinding in accordance with one embodiment of the present disclosure can have a moisture content ranging from about 40% to about 60%, or from about 40% to about 55%, or below 50%. It will be appreciated by one of ordinary skill in the art that the moisture content of dewatered wet ground carbonaceous materials depends on the particular type of carbonaceous materials, the particle size distribution, and the particular dewatering equipment used. Such filter cakes can be thermally treated to produce one or more reduced moisture carbonaceous particulates.

Each of the one or more carbonaceous particulates can have a unique composition, as described above. For example, two carbonaceous particulates can be utilized, where a first carbonaceous particulate comprises one or more biomass materials and the second carbonaceous particulate comprises one or more non-biomass materials. Alternatively, a single carbonaceous particulate comprising one or more carbonaceous materials utilized.

Catalyst Loading for Hydromethanation (350)

The hydromethanation catalyst is potentially active for catalyzing at least reactions (I), (II) and (III) described above. Such catalysts are in a general sense well known to those of ordinary skill in the relevant art and may include, for example, alkali metals, alkaline earth metals and transition metals, and compounds and complexes thereof. Typically, the hydromethanation catalyst comprises at least an alkali metal, such as disclosed in many of the previously incorporated references.

For the hydromethanation reaction, the one or more carbonaceous particulates are typically further processed to associate at least one hydromethanation catalyst, typically comprising a source of at least one alkali metal, to generate a catalyzed carbonaceous feedstock (31+32). If a liquid carbonaceous material is used, the hydromethanation catalyst may for example be intimately mixed into the liquid carbonaceous material.

The carbonaceous particulate provided for catalyst loading can be either treated to form a catalyzed carbonaceous feedstock (31+32) which is passed to the hydromethanation reactor (200), or split into one or more processing streams, where at least one of the processing streams is associated with a hydromethanation catalyst to form at least one catalyst-treated feedstock stream. The remaining processing streams can be, for example, treated to associate a second component therewith. Additionally, the catalyst-treated feedstock stream can be treated a second time to associate a second component therewith. The second component can be, for example, a second hydromethanation catalyst, a co-catalyst, or other additive.

In one example, the primary hydromethanation catalyst (alkali metal compound) can be provided to the single carbonaceous particulate (e.g., a potassium and/or sodium source), followed by a separate treatment to provide one or more co-catalysts and additives (e.g., a calcium source) to the same single carbonaceous particulate to yield the catalyzed carbonaceous feedstock (31+32). For example, see previously incorporated US2009/0217590A1 and US2009/0217586A1.

The hydromethanation catalyst and second component can also be provided as a mixture in a single treatment to the single second carbonaceous particulate to yield the catalyzed carbonaceous feedstock (31+32).

When one or more carbonaceous particulates are provided for catalyst loading, then at least one of the carbonaceous particulates is associated with a hydromethanation catalyst to form at least one catalyst-treated feedstock stream. Further, any of the carbonaceous particulates can be split into one or more processing streams as detailed above for association of a second or further component therewith. The resulting streams can be blended in any combination to provide the catalyzed carbonaceous feedstock (31+32), provided at least one catalyst-treated feedstock stream is utilized to form the catalyzed feedstock stream.

In one embodiment, at least one carbonaceous particulate is associated with a hydromethanation catalyst and optionally, a second component. In another embodiment, each carbonaceous particulate is associated with a hydromethanation catalyst and optionally, a second component.

Any methods known to those skilled in the art can be used to associate one or more hydromethanation catalysts with any of the carbonaceous particulates and/or processing streams. Such methods include but are not limited to, admixing with a solid catalyst source and impregnating the catalyst onto the processed carbonaceous material. Several impregnation methods known to those skilled in the art can be employed to incorporate the hydromethanation catalysts. These methods include but are not limited to, incipient wetness impregnation, evaporative impregnation, vacuum impregnation, dip impregnation, ion exchanging, and combinations of these methods.

In one embodiment, an alkali metal hydromethanation catalyst can be impregnated into one or more of the carbonaceous particulates and/or processing streams by slurrying with a solution (e.g., aqueous) of the catalyst in a loading tank. When slurried with a solution of the catalyst and/or co-catalyst, the resulting slurry can be dewatered to provide a catalyst-treated feedstock stream, again typically, as a wet cake. The catalyst solution can be prepared from any catalyst source in the present processes, including fresh or make-up catalyst and recycled catalyst or catalyst solution. Methods for dewatering the slurry to provide a wet cake of the catalyst-treated feedstock stream include filtration (gravity or vacuum), centrifugation, and a fluid press.

In another embodiment, as disclosed in previously incorporated US2010/0168495A1, the carbonaceous particulates are combined with an aqueous catalyst solution to generate a substantially non-draining wet cake, then mixed under elevated temperature conditions and finally dried to an appropriate moisture level.

One particular method suitable for combining a coal particulate and/or a processing stream comprising coal with a hydromethanation catalyst to provide a catalyst-treated feedstock stream is via ion exchange as described in previously incorporated US2009/0048476A1 and US2010/0168494A1. Catalyst loading by ion exchange mechanism can be maximized based on adsorption isotherms specifically developed for the coal, as discussed in the incorporated reference. Such loading provides a catalyst-treated feedstock stream as a wet cake. Additional catalyst retained on the ion-exchanged particulate wet cake, including inside the pores, can be controlled so that the total catalyst target value can be obtained in a controlled manner. The total amount of catalyst loaded can be controlled by controlling the concentration of catalyst components in the solution, as well as the contact time, temperature and method, as disclosed in the aforementioned incorporated references, and as can otherwise be readily determined by those of ordinary skill in the relevant art based on the characteristics of the starting coal.

In another example, one of the carbonaceous particulates and/or processing streams can be treated with the hydromethanation catalyst and a second processing stream can be treated with a second component (see previously incorporated US2007/0000177A1).

The carbonaceous particulates, processing streams, and/or catalyst-treated feedstock streams resulting from the preceding can be blended in any combination to provide the catalyzed second carbonaceous feedstock, provided at least one catalyst-treated feedstock stream is utilized to form the catalyzed carbonaceous feedstock (31+32). Ultimately, the catalyzed carbonaceous feedstock (31+32) is passed onto the hydromethanation reactor(s) (200).

Generally, each catalyst loading unit comprises at least one loading tank to contact one or more of the carbonaceous particulates and/or processing streams with a solution comprising at least one hydromethanation catalyst, to form one or more catalyst-treated feedstock streams. Alternatively, the catalytic component may be blended as a solid particulate into one or more carbonaceous particulates and/or processing streams to form one or more catalyst-treated feedstock streams.

Typically, when the hydromethanation catalyst is solely or substantially an alkali metal, it is present in the catalyzed carbonaceous feedstock in an amount sufficient to provide a ratio of alkali metal atoms to carbon atoms in the catalyzed carbonaceous feedstock ranging from about 0.01, or from about 0.02, or from about 0.03, or from about 0.04, to about 0.10, or to about 0.08, or to about 0.07, or to about 0.06.

Suitable alkali metals are lithium, sodium, potassium, rubidium, cesium, and mixtures thereof. Particularly useful are potassium sources. Suitable alkali metal compounds include alkali metal carbonates, bicarbonates, formates, oxalates, amides, hydroxides, acetates, or similar compounds. For example, the catalyst can comprise one or more of sodium carbonate, potassium carbonate, rubidium carbonate, lithium carbonate, cesium carbonate, sodium hydroxide, potassium hydroxide, rubidium hydroxide or cesium hydroxide, and particularly, potassium carbonate and/or potassium hydroxide.

Optional co-catalysts or other catalyst additives may be utilized, such as those disclosed in the previously incorporated references.

The one or more catalyst-treated feedstock streams that are combined to form the catalyzed carbonaceous feedstock typically comprise greater than about 50%, greater than about 70%, or greater than about 85%, or greater than about 90% of the total amount of the loaded catalyst associated with the catalyzed carbonaceous feedstock (31+32). The percentage of total loaded catalyst that is associated with the various catalyst-treated feedstock streams can be determined according to methods known to those skilled in the art. Separate carbonaceous particulates, catalyst-treated feedstock streams, and processing streams can be blended appropriately to control, for example, the total catalyst loading or other qualities of the catalyzed carbonaceous feedstock (31+32), as discussed previously. The appropriate ratios of the various stream that are combined will depend on the qualities of the carbonaceous materials comprising each as well as the desired properties of the catalyzed carbonaceous feedstock (31+32). For example, a biomass particulate stream and a catalyzed non-biomass particulate stream can be combined in such a ratio to yield a catalyzed carbonaceous feedstock (31+32) having a predetermined ash content, as discussed previously.

Any of the preceding catalyst-treated feedstock streams, processing streams, and processed feedstock streams, as one or more dry particulates and/or one or more wet cakes, can be combined by any methods known to those skilled in the art including, but not limited to, kneading, and vertical or horizontal mixers, for example, single or twin screw, ribbon, or drum mixers. The resulting catalyzed carbonaceous feedstock (31+32) can be stored for future use or transferred to one or more feed operations for introduction into the hydromethanation reactor(s). The catalyzed carbonaceous feedstock can be conveyed to storage or feed operations according to any methods known to those skilled in the art, for example, a screw conveyer or pneumatic transport.

In one embodiment, the carbonaceous feedstock as fed to the hydromethanation reactor contains an elevated moisture content of from greater than 10 wt %, or about 12 wt % or greater, or about 15 wt % or greater, to about 25 wt % or less, or to about 20 wt % or less (based on the total weight of the carbonaceous feedstock), to the extent that the carbonaceous feedstock is substantially free-flowing (see previously incorporated US2012/0102837A1).

The term "substantially free-flowing" as used herein means the carbonaceous feedstock particulates do not agglomerate under feed conditions due to moisture content. Desirably, the moisture content of the carbonaceous feedstock particulates is substantially internally contained so that there is minimal (or no) surface moisture.

A suitable substantially free-flowing catalyzed carbonaceous feedstock (31+32) can be produced in accordance with the disclosures of previously incorporated US2010/0168494A1 and US2010/0168495A1, where the thermal treatment step (after catalyst application) referred to in those disclosures can be minimized (or even potentially eliminated).

To the extent necessary, excess moisture can be removed from the catalyzed carbonaceous feedstock (31+32). For example, the catalyzed carbonaceous feedstock (31+32) may be dried with a fluid bed slurry drier (i.e., treatment with superheated steam to vaporize the liquid), or the solution thermally evaporated or removed under a vacuum, or under a flow of an inert gas, to provide a catalyzed carbonaceous feedstock having a the required residual moisture content.

Gas Processing

Heat Exchanger System (400) and High-Pressure Steam Stream (40)

Figure 4:
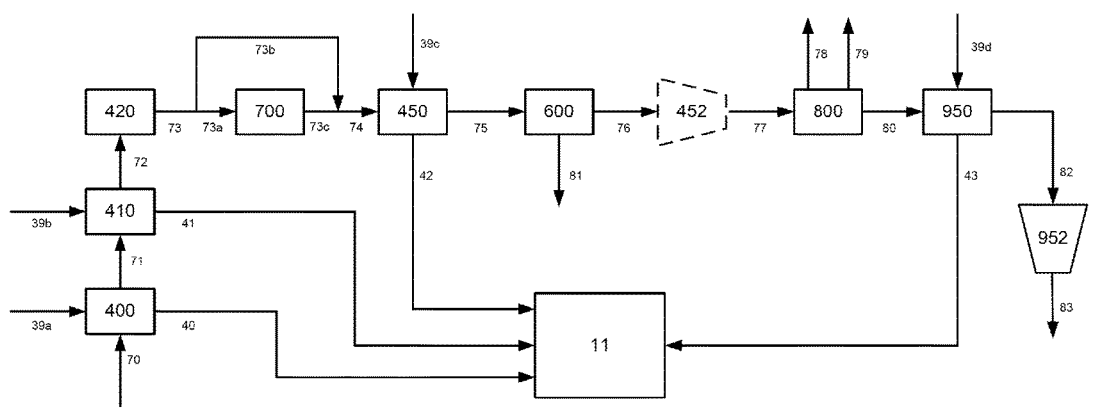
FIG. 4 is a diagram of a representative embodiment for the further processing of the fines-cleaned methane-enriched raw product stream to make a pipeline-quality substitute natural gas (SNG).

The fines-cleaned methane-enriched raw product gas stream (70) leaving the hydromethanation reactor (200) contains a very small amount of fines after being processed by the highly-efficient system of cyclones. FIG. 4 illustrates the further processing of the methane-enriched raw product gas stream to make the final product, i.e., pipeline-quality substitute natural gas (SNG).

The temperature and pressure of stream (70) are dictated by the chosen operating conditions. The pressure ranges from 250 to 1000 psig (1825 to 6996 kPa) and is preferably between 500 and 650 psig (3549 to 4583 kPa). The temperature ranges from 1100 to 1500° F. (593 to 816° C.) and is preferably between 1250 and 1350° F. (677 to 732° C.).

Referring to FIG. 4, fines-cleaned methane-rich raw product gas stream (70) is routed to a heat exchanger or boiler system (400), optionally comprising a superheater section (not shown), to recover thermal energy in the form of high-pressure steam stream (40) by vaporization of boiler feed water (39a). The pressure of the steam is at least 25 to 50 psig (172 to 345 kPa) higher than the pressure of the hydromethanation reactor (200). Steam stream (40) is preferably superheated to 750 to 950° F. (399 to 510° C.) to maximize the thermal efficiency of the hydromethanation reactor (200). In the absence of the superheater section of heat exchanger system (400) saturated steam may be produced at the pressure stated above for heat exchanger system (400), if required. Steam stream (40) is sent to the steam distribution system (11).

Cooled methane-enriched raw product stream (71) is the methane-enriched raw product leaving the heat exchanger system (400) that has been cooled to about 550° F. (288° C.). It is further cooled against boiler feed water (39b) to 370-400° F. (188 to 204° C.) in intermediate-pressure heat exchanger or boiler (410) to generate intermediate-pressure saturated steam (41) at 150 psig (1136 kPa), which is close to the dew point of syngas under those conditions. Intermediate-pressure saturated steam stream (41) is sent to the steam distribution system (11).

Methane-enriched raw product gas stream (72) leaving intermediate-pressure boiler (410) is scrubbed in a hot gas scrubber (420) with recycled process condensate (not shown), which is obtained from an ammonia recovery system (600) (as discussed below), to remove any traces of fine particulate matter that has escaped the cyclones. A bleed stream (not shown) from the hot gas scrubber (420) containing the fine particulate matter is routed to the catalyst recovery system (300) (not shown). A particle-free cooled gas (73) exits the hot gas scrubber (420).

Gas Conversion/Purification

Referring to FIG. 4, raw product conversion/purification will typically comprise water-gas shift reactors (700), low temperature gas cooling (450), ammonia recovery (600), acid gas removal (800) and methanation (950).

Water-Gas Shift System (700)

The particle-free cooled gas stream (73) exiting the hot gas scrubber (420) is split into two streams, a shift inlet stream (73a) and a shift bypass stream (73b). Shift inlet stream (73a) is sent to the water-gas shift system (700) where a portion of the stream is reheated to 450 to 550° F. (232 to 288° C.) and then passed over a sour-shift catalyst (typically cobalt-molybdenum) in a fixed bed reactor to convert a portion of the carbon monoxide and steam to hydrogen and carbon dioxide, forming shift outlet stream (73c). Since the shift reaction is exothermic, the shift outlet stream (73c) from the shift reactor exchanges heat with shift inlet stream (73a) to recover energy. Shift bypass stream (73b) bypasses water-gas shift system (700) and is combined with shift outlet stream (73c) to form hydrogen-enriched raw product gas stream (74). The fraction of particle-free cooled gas (73) that is shifted is controlled to maintain a ratio hydrogen to carbon monoxide of approximately 3:1 in the combined gas stream (74).

Methods and reactors for performing the water-gas shift reaction on a CO-containing gas stream are well known to those of skill in the art. An example of a suitable shift reactor is illustrated in U.S. Pat. No. 7,074,373, hereby incorporated by reference, although other designs known to those of skill in the art are also effective.

Low-Temperature Gas Cooling (450)

After leaving the water-gas shift reactor system (700), hydrogen-enriched raw product gas stream (74) is cooled in a series of heat exchangers within low-temperature gas cooling system (450) to further reduce the temperature to 120° F. (49° C.) to produce a dry raw gas stream (75). The low-temperature gas cooling system (450) will typically comprise first and second knock-out drums, an air cooler, and a trim cooler.

Hydrogen-enriched raw product gas stream (74), initially at about 475° F. (246° C.), is first cooled against boiler feed water (39c) to generate medium-pressure steam (42) at 50 psig (446 kPa) and low-pressure steam (not shown) at two levels: 30 psig (308 kPa) and 15 psig (205 kPa). Recovery of low-grade heat allows heat integration with other parts of the process where steam at these pressure levels is needed. Medium-pressure steam stream (42) is sent to the steam distribution system (11). As the gas (74) is cooled down to 200° F. (93° C.), it begins to approach the water dew-point and the condensing water is recovered in a first knock-out drum (not shown). Subsequent cooling of gas (74) takes place against the air cooler (not shown), which uses ambient air as a cooling medium, and finally the trim cooler (not shown), to achieve a final temperature of 120° F. (49° C.) using cooling water. Ambient conditions at the location of the low-temperature gas cooling system (450) will dictate the amount of air cooling and trim cooling that can be achieved. The stream leaving the trim cooler is sent to the second knock-out drum (not shown) to separate the remaining water from the gas (74). The combined condensate from the knock-out drums (not shown) is sent to the ammonia recovery system (600). Dry raw gas stream (75) exits the low-temperature gas cooling system (450).

Ammonia Recovery System (600)

The low-temperature operation of the hydromethanation reactor (200) under highly reducing conditions relative to other gasification technologies allows all the nitrogen released as ammonia during devolatilization to remain in molecular form without converting to other nitrogen oxides or decomposing to gaseous nitrogen. Ammonia can be recovered according to methods known to those skilled in the art. A particular embodiment of the ammonia recovery process is described next.

Referring to FIG. 4, after dry raw gas stream (75) exits low-temperature gas cooling system (450) it is treated in an ammonia recovery system (600) to form ammonia-free dry raw gas stream (76). Ammonia recovery system (600) will typically comprise a series of sour water strippers and a Claus unit. Ammonia is recovered from dry raw gas stream (75) by first washing dry raw gas stream (75) with chilled water at 50° F. (10° C.) to remove a majority of the ammonia. The resulting ammonia scrubber bottoms liquid is combined with the condensate from the knock-out drums and fed to a series of sour water strippers (not shown) that separate the ammonia from liquid-phase as a primary product stream and an off-gas containing trace amounts of ammonia, hydrogen cyanide, hydrogen sulfide and carbonyl sulfide. The off-gas stream is sent to the Claus unit (not shown) for further treatment. The ammonia recovery system (600) also produces a condensate (not shown) which is recycled to hot gas scrubber (420).

The clean water leaving the sour-water strippers is devoid of dissolved gases. A portion of this water is utilized as a liquid feed for the hot gas scrubber (420). The balance of the water is sent to the catalyst recovery system (300) as a solvent for the char washing step (not shown).

Ammonia recovery is greater than 95% of the ammonia contained in the methane-rich raw gas stream. Ammonia is typically recovered as an aqueous solution (81) of concentration 20-30 wt %. Any recovered ammonia can be used as such or, for example, can be converted with other by-products from the process. For example, it may be reacted with sulfuric acid to generate ammonium sulfate as a product.

Optional Booster Compressor Unit (452)

After exiting ammonia recovery system (600), ammonia-free dry raw gas stream (76) may optionally be compressed prior to treatment in acid gas removal unit (800) to generate a compressed ammonia-free dry raw gas stream (77), as disclosed in previously incorporated US2012/0305848A1. A booster compressor unit (452) compresses the stream to a pressure which is higher than ammonia-free dry raw gas stream (76), and much higher than the operating pressure of hydromethanation reactor (200).

The purpose of the booster compressor unit (452) is to take advantage of the higher efficiency of removal of $CO_2$ at higher pressures using physical absorbents such as refrigerated methanol. At the same time, the hydromethanation reactor (200) may be operated at a lower pressure that is optimal for catalytic gasification and does not require the entire front-end of the process to be designed for a higher operating pressure. Although the volume of ammonia-free dry raw gas stream (76) is higher than that of the final methane-enriched product stream (82) from the methanation system (950), the increased power consumption of booster compressor (452) can be partially offset by the elimination of a final product compressor (952). For example, the hydromethanation reactor (200) can be operated at 500 psig (3549 kPa) and booster compressor (452) can raise the pressure of compressed ammonia-free dry raw gas stream (77) to 1050-1100 psig (7341-7686 kPa).

Booster compressor unit (452) can be a single or series of gas compressors depending on the required extent of compression, as will be understood by a person of ordinary skill in the art. Suitable types of compressors are also generally well known to those of ordinary skill in the art, for example, compressors known to be suitable for use with syngas streams (carbon monoxide plus hydrogen) would also be suitable for use in connection with the present process.

As indicated above, compressed ammonia-free dry raw gas stream (77) is at a pressure higher than ammonia-free dry raw gas stream (76). In one embodiment, the pressure of compressed ammonia-free gas raw gas stream (77) is about 20% higher or greater, or about 35% higher or greater, or about 50% higher or greater, to about 100% higher or less, than the pressure of ammonia-free dry raw gas stream (76).

In another embodiment, the pressure of compressed ammonia-free gas raw gas stream (77) is about 720 psig (5066 kPa) or greater, or about 750 psig (5272 kPa) or greater, and about 1000 psig (6996 kPa) or less, or about 900 psig (6307 kPa) or less, or about 850 psig (5962 kPa) or less.

In another embodiment, the pressure of ammonia-free dry raw gas stream (76) is about 600 psig (4238 kPa) or less, or about 550 psig (3893 kPa) or less, or about 500 psig (3549 kPa) or less, and about 400 psig (2860 kPa) or greater, or about 450 psig (3204 kPa) or greater.

Acid Gas Removal System (800)

The ammonia-free dry raw gas stream (76) leaving the ammonia recovery system (600) (or the compressed ammonia-free gas raw gas stream (77) leaving the optional booster compressor unit (452), if present) is subsequently fed to an acid gas removal (AGR) unit (800) to remove a substantial portion of $CO_2$ and a substantial portion of the $H_2S$ and generate a sweetened gas stream (80).

Acid gas removal processes typically involve contacting a gas stream with a solvent that selectively absorbs the acid gases. Several acid gas removal processes are commercially available and applicable for treatment of streams (76) or (77). The main criteria for selection of the AGR are minimization of methane losses such that the sweetened gas stream (80) comprises at least a substantial portion (and substantially all) of the methane from the stream fed into acid gas removal unit (800). Typically, such losses should be about 2 mol % or less, or about 1.5 mol % or less, or about 1 mol % of less, respectively, of the methane feed to the AGR.

A solvent that meets the above criteria is refrigerated methanol. A commercially available process employing methanol as solvent is known by the trade-name Rectisol® and is offered by Linde AG and Lurgi Oel-Gas-Chemie GmbH. Another commercial process that may be considered is Selexol® (UOP LLC, Des Plaines, Ill. USA), which uses a proprietary solvent (dimethyl ether of polyethylene glycol). Similarly, a chemical solvent comprised of methyldiethanolamine (MDEA) with other additives such as piperazine may also be used. MDEA is available from process licensors such as BASF and Dow.

One method for removing acid gases is described in previously incorporated US2009/0220406A1.

At least a substantial portion (e.g., substantially all) of the $CO_2$ and/or $H_2S$ (and other remaining trace contaminants) should be removed via the acid gas removal processes. "Substantial" removal in the context of acid gas removal means removal of a high enough percentage of the component such that a desired end product can be generated. The actual amounts of removal may thus vary from component to component. For "pipeline-quality natural gas", only trace amounts (at most) of $H_2S$ can be present, although higher (but still small) amounts of $CO_2$ may be tolerable.

The resulting sweetened gas stream (80) will generally comprise $CH_4$, $H_2$ and CO (for the downstream methanation), and typically traces of $H_2O$.

Any recovered $H_2S$ (78) from the acid gas removal (and other processes such as sour water stripping) can be converted to elemental sulfur by any method known to those skilled in the art, including the Claus process. Sulfur can be recovered as a molten liquid.

Any recovered $CO_2$ (79) from the acid gas removal can be compressed for transport in $CO_2$ pipelines, industrial use, and/or sequestration for storage or other processes such as enhanced oil recovery and can also be used for other process operations (such as in certain aspects catalyst recovery and feed preparation).

The resulting sweetened gas stream (80) can be further processed as described below to produce pipeline quality SNG.

Methanation System (950)

The sweetened gas stream (80) is fed to a methanation system (950) to generate additional methane from the carbon monoxide and hydrogen that may be present in those streams, resulting in a methane-enriched product stream (82).

The methanation system (950) will typically comprise one or more methanation reactors or catalytic methanators (not shown), e.g., a single-stage methanation reactor, a series of single-stage methanation reactors or a multistage reactor. Methanation reactors include, without limitation, fixed bed, moving bed or fluidized bed reactors. See, for instance, U.S. Pat. Nos. 3,958,957, 4,252,771, 3,996,014 and 4,235,044. Methanation reactors and catalysts are generally commercially available. The catalyst used in the methanation, and methanation conditions, are generally known to those of ordinary skill in the relevant art, and will depend, for example, on the temperature, pressure, flow rate and composition of the incoming gas stream.

The methanation system (950) will also typically comprise a heat recovery system with heat exchanger units. As the methanation reaction is highly exothermic, the heat recovery system generates high-pressure, superheated or saturated steam in the heat exchanger units to remove a portion of the heat energy. The recovered heat energy is utilized to generate a high-pressure steam stream (43) from boiler feed water (39d).

A final product compressor (952) raises the pressure of the methane-enriched product stream (82) from the methanation system (950) to the required pipeline pressure to form a pipeline quality SNG (83). Alternatively, the methane-enriched product stream (82) can be further processed, when necessary, to separate and recover $CH_4$ by any suitable gas separation method known to those skilled in the art including, but not limited to, cryogenic distillation and the use of molecular sieves or gas separation (e.g., ceramic) membranes. Additional gas purification methods include, for example, the generation of methane hydrate as disclosed in previously incorporated US2009/0260287A1, US2009/0259080A1 and US2009/0246120A1.

Pipeline Quality Natural Gas

The processes and systems described are capable of generating "pipeline-quality natural gas" (or "pipeline-quality substitute natural gas") from the hydromethanation of non-gaseous carbonaceous materials. A "pipeline-quality natural gas" typically refers to a methane-containing stream that meets the conditions in Table 1:

TABLE 1

| Parameter | Value | Units | Source |
|---|---|---|---|
| Higher Heating Value (HHV) | >35.367 | MJ/Nm³ | 1 |
|  | >950 | BTU/scf | 1 |
| Wobbe Index (WI) | >46.1-56.5 | MJ/Nm³ | 2 |
| Relative Density | 0.55-0.70 | — | 2 |
| Sulfur Content | <0.0023 | kg/100 Nm³ | 1 |
|  | <0.00014 | lb/100 scf | 1 |
| $CO_2$ Content | <2 | vol. % | 1 |
| Moisture Content | <62.5 | kg/1000 Nm³ | 1 |
|  | <3.9 | lb/1000 scf | 1 |
| Temperature | <49 (120) | ° C. (° F.) | 1 |
| Toxic/Corrosive contaminants | None | — | 1 |

The specification for the product quality of SNG in terms of gas composition is listed in Table 2:

TABLE 2

| Component | Value | Units |
|---|---|---|
| $CH_4$ | 94-98 | mol % |
| $H_2$ | <2 | mol % |
| CO | <100 | ppmv |
| $CO_2$ | <97 | ppmv |

In the process described, the pipeline quality SNG (83) satisfies the specification of Tables 1 and 2.

Steam Generation and Distribution System

The hydromethanation process requires steam at several different pressures. First, steam is needed as a reactant in the hydromethanation reactor (200). Steam is fed to the hydromethanation reactor (200) at a pressure that is higher than the reactor pressure by at least 50 psig (446 kPa). Although the reactor can be operated with saturated steam, an energy penalty in terms of increased oxygen use, decreased methane production and increased carbon dioxide production must be incurred. As a result, superheated steam at 510° C. (950° F.) at the required pressure is preferred to maximize the overall process thermal efficiency. Second, steam is required as a utility to perform various heating duties such as evaporation/crystallization of catalyst solution, reboiler for the AGR and ammonia recovery system, etc.

Referring to FIG. 4, the steam distribution system (11) receives the steam generated by various sources and distributes them to consumers within the process. The main process heat exchanger or boiler (400) following the hydromethanation reactor (200) and the heat exchanger units within the methanation system (950) produce high pressure steam of the required quality for the hydromethanation reactor (200). As discussed previously, the temperature of the steam is normally maximized to improve efficiency. The hydromethanation reactor (200) steam requirements, supplied by steam stream (12), are met by distributing high-pressure steam streams (40 and 43), via steam distribution system (11). The high-pressure, saturated or superheated steam in excess of the hydromethanation reactor (200) requirements is let down in pressure to a level of 50 psig (446 kPa). The saturated steam from the intermediate pressure boiler (410) at 150 psig (1136 kPa) is also let down in pressure to a level of 50 psig (446 kPa). The low-temperature gas cooling system (450) also produces medium-pressure (50 psig) steam (42) by recovery of lower grade heat. All sources of 50 psig steam serve as a heat-transfer media for various consumers within the process. Excess 50 psig (446 kPa) steam is let down to 30 psig (304 kPa) and combines with sources of 30 psig (304 kPa) steam within the low temperature gas cooling to be distributed to various consumers within the process. The various steam sources produce sufficient steam at the required levels to meet the requirements of various consumers. As a result, the overall process is steam balanced. Any high-pressure steam in excess of process requirements may be converted to power as described below. The process has a steam demand and a power demand that are met by internal energy integration such that the process requires no net import of steam or power.

Power Generation System

As shown in FIG. 2, a gas turbine combined cycle system, comprising an air compressor (991), a high-pressure gas turbine combustion chamber (992), a gas expander (993) and a heat recovery steam generator (975), is employed to generate electric power from the low or medium BTU oxidation reactor product gas (88) exiting the oxidation reactor (380) operated at a high pressure. The gas turbine combined cycle system generates power by burning gas (88) with atmospheric air (90) at elevated pressure (typically about 10 bar) in the combustion chamber (992) and expanding the combustion gases through the gas expander (993). As the gas expands and cools, it drives the gas expander which in turn will power the air compressor (991) and electric generator (99a). The amount of gross power generated depends on the pressure, temperature, volume and molecular weight of the combustion gases and the efficiency of the gas expander. The net power generated is calculated by subtracting the power needed to compress the air and the efficiency losses of the electric generator from the gross power generated by the gas expander.

If the oxidation reactor product gas (88) is pressurized but has no chemical heating value since it is comprised of $CO_2$, steam and nitrogen, some work and electric power can still be recovered by expanding the hot oxidation reactor product gas (88) through the gas expander (993) coupled to an electric generator (99a) as shown in FIG. 3.

The expander exhaust gas (97) contains sufficient thermal energy to produce steam and subsequently more power. The expander exhaust gas (97) typically is above 454° C. (850° F.) and may be used to generate superheated steam in the heat recovery steam generator (975). The heat recovery steam generator (975) is an insulated low-pressure vessel with an arrangement of tubes and coils that are designed to efficiently cool the exhaust gas and convert boiler feed water into steam. Sometimes the heat recovery steam generator (975) is equipped with burners to provide supplemental heat in order to increase the temperature and/or pressure of the steam.

The steam produced in the heat recovery steam generator (975) is directed to a steam-turbine generator which comprises a steam turbine (980) that drives an electric generator (99b). The steam turbine may include any number of stages whereby some steam may be extracted at different pressures and temperatures, if desired. In addition, the extracted steam can be re-heated and injected into a subsequent stage to improve the net power generated by the steam turbine.

The electrical generators can be of any kind, AC or DC, that are widely used today. All electrical generators fundamentally consist of two parts: (1) electro-magnets or permanent magnets that produce a magnetic flux and (2) a laminated steel core that carrying conductors. The relative motion between the conductors and magnetic field produces a voltage in accordance to Faraday's law.

Water Treatment and Recovery

Residual contaminants in waste water resulting from any one or more of the trace contaminant removal, sour shift, ammonia removal, acid gas removal and/or catalyst recovery processes can be removed in a waste water treatment unit (not shown) to allow recycling of the recovered water within the plant and/or disposal of the water from the plant process according to any methods known to those skilled in the art. Depending on the feedstock and reaction conditions, such residual contaminants can comprise, for example, aromatics, CO, $CO_2$, $H_2S$, COS, HCN, $NH_3$, and Hg. For example, $H_2S$ and HCN can be removed by acidification of the waste water to a pH of about 3, treating the acidic waste water with an inert gas in a stripping column, and increasing the pH to about 10 and treating the waste water a second time with an inert gas to remove ammonia (see U.S. Pat. No. 5,236,557). $H_2S$ can be removed by treating the waste water with an oxidant in the presence of residual coke particles to convert the H$_2$S to insoluble sulfates which may be removed by flotation or filtration (see U.S. Pat. No. 4,478,725). Aromatics can be removed by contacting the waste water with a carbonaceous char optionally containing mono- and divalent basic inorganic compounds (e.g., the solid char product or the depleted char after catalyst recovery, supra) and adjusting the pH (see U.S. Pat. No. 4,113,615). Trace amounts of aromatics (C$_6$H$_6$, C$_7$H$_8$, C$_{10}$H$_8$) can also be removed by extraction with an organic solvent followed by treatment of the waste water in a stripping column (see U.S. Pat. Nos. 3,972,693, 4,025,423 and 4,162,902).

Multi-Train Processes

Each process may be performed in one or more processing units. For example, one or more hydromethanation reactors may be supplied with the carbonaceous feedstock from one or more catalyst loading and/or feedstock preparation unit operations. Similarly, the methane-enriched raw product streams generated by one or more hydromethanation reactors may be processed or purified separately or via their combination at various downstream points depending on the particular system configuration, as discussed, for example, in previously incorporated US2009/0324458A1, US2009/0324459A1, US2009/0324460A1, US2009/0324461A1 and US2009/0324462A1.

In certain embodiments, the processes utilize two or more hydromethanation reactors (e.g., 2-4 hydromethanation reactors). In such embodiments, the processes may contain divergent processing units (i.e., less than the total number of hydromethanation reactors) prior to the hydromethanation reactors for ultimately providing the catalyzed carbonaceous feedstock to the plurality of hydromethanation reactors, and/or convergent processing units (i.e., less than the total number of hydromethanation reactors) following the hydromethanation reactors for processing the plurality of methane-enriched raw product streams generated by the plurality of hydromethanation reactors.

When the systems contain convergent processing units, each of the convergent processing units can be selected to have a capacity to accept greater than a 1/n portion of the total feed stream to the convergent processing units, where n is the number of convergent processing units. Similarly, when the systems contain divergent processing units, each of the divergent processing units can be selected to have a capacity to accept greater than a 1/m portion of the total feed stream supplying the convergent processing units, where m is the number of divergent processing units.

While a number of example embodiments have been provided, the various aspects and embodiments disclosed herein are for purposes of illustration and are not intended to be limiting. Other embodiments can be used, and other changes can be made, without departing from the spirit and scope of the subject matter presented herein. It will be readily understood that the aspects of the disclosure, as generally described herein, and illustrated in the figures, can be arranged, substituted, combined, separated, and designed in a wide variety of different configurations, all of which are explicitly contemplated herein.

We claim:

1. A process for generating, from a non-gaseous carbonaceous material and a hydromethanation catalyst, (1) a fines-cleaned methane-enriched raw product gas stream, (2) an oxidation reactor product gas and (3) an oxidation reactor ash product stream, the process comprising the steps of:
  a) preparing a carbonaceous feedstock from the non-gaseous carbonaceous material;
  b) introducing the carbonaceous feedstock, the hydromethanation catalyst, steam and oxygen into a hydromethanation reactor, the hydromethanation reactor comprising a fluidized bed, a disengagement zone above the fluidized bed, and a gas mixing zone below the fluidized bed;
  c) reacting the carbonaceous feedstock in the hydromethanation reactor in the presence of carbon monoxide, hydrogen, steam and hydromethanation catalyst, and at an operating temperature from about 400° F. (about 205° C.) up to about 1500° F. (about 816° C.), and an operating pressure of at least about 250 psig (about 1825 kPa), to produce a methane-enriched raw product gas, heat energy and a by-product char;
  d) withdrawing a stream of methane-enriched raw product gas from the hydromethanation reactor as the methane-enriched raw product gas stream, wherein the methane-enriched raw product gas stream comprises methane, carbon monoxide, hydrogen, carbon dioxide, hydrogen sulfide, steam, and entrained solids;
  e) removing a substantial portion of the entrained solids from the methane-enriched raw product gas stream to generate a solids-depleted, methane-enriched raw product gas stream and a recovered primary solids stream;
  f) removing a substantial portion of any fines from the solids-depleted, methane-enriched raw product gas stream to generate the fines-cleaned methane-enriched raw product gas stream and a recovered secondary fines stream;
  g) withdrawing a stream of by-product char from the hydromethanation reactor as the hydromethanation reactor char product stream, wherein the hydromethanation reactor char product stream comprises a carbon content and entrained hydromethanation catalyst;
  h) extracting a portion of the entrained catalyst from the hydromethanation reactor char product stream by the steps of:
    (i) feeding all or a portion of the hydromethanation reactor char product stream to a catalyst recovery unit;
    (ii) withdrawing a stream of catalyst-depleted char from the catalyst recovery unit as the washed char product stream, the washed char product stream comprising a carbon content; and
    (iii) withdrawing a stream of liberated hydromethanation catalyst from the catalyst recovery unit as a recovered hydromethanation catalyst stream;
  i) feeding into an oxidation reactor (1) all or a portion of the washed char product stream, and (2) an oxygen-containing gas stream;
  j) reacting at least a portion of the carbon content of the washed char product stream with the oxygen-containing gas stream in the oxidation reactor to produce (1) an oxidation reactor ash product stream, and (2) an oxidation reactor product gas comprising steam and carbon dioxide; and
  k) withdrawing the oxidation reactor product gas from the oxidation reactor.

2. The process of claim 1, further comprising the steps of:
  (A) operating the oxidation reactor at a pressure greater than 791 kPa (100 psig);
  (B) (i) when the oxidation reactor product gas further comprises carbon monoxide and hydrogen, feeding all or a portion of the oxidation reactor product gas into a gas turbine combined cycle system to generate power and steam; or (ii) when carbon monoxide and hydrogen are not present in the oxidation reactor product gas, feeding all or a portion of the oxidation reactor product gas into a gas expander and a heat recovery steam generator to generate power and steam; and (C) cooling or quenching the oxidation reactor ash product stream.

3. The process of claim 1, further comprising the steps of:
(A) operating the oxidation reactor at a pressure less than 400 kPa (44 psig);
(B) (i) when the oxidation reactor product gas further comprises carbon monoxide and hydrogen, feeding all or a portion of the oxidation reactor product gas to a heat recovery steam generator equipped with an auxiliary burner to generate steam; or
(ii) when carbon monoxide and hydrogen are not present in the oxidation reactor product gas, feeding all or a portion of the oxidation reactor product gas to a heat recovery steam generator to generate steam; and
(C) cooling or quenching the oxidation reactor ash product stream.

4. The process of claim 2, further comprising the steps of (D) converting all or a portion of the steam generated in step (B) to power in a steam-turbine generator, and (E) exporting any unused steam.

5. The process of claim 3, further comprising the steps of (D) converting all or a portion of the steam generated in step (B) to power in a steam-turbine generator, and (E) exporting any unused steam.

6. The process of claim 1, wherein the operating pressure in the hydromethanation reactor ranges from at least about 250 psig (about 1825 kPa) up to about 1200 psig (about 8375 kPa).

7. The process of claim 1, wherein the oxidation reactor is a fluidized-bed oxidation reactor.

8. The process of claim 1, wherein the hydromethanation catalyst comprises an alkali metal.

9. The process of claim 8, wherein the alkali metal is potassium.

10. The process of claim 1, further comprising the steps of:
(f1) feeding the recovered primary solids stream into the hydromethanation reactor; and
(f2) feeding all or a portion of the recovered secondary fines stream into the catalyst recovery unit.

11. The process of claim 1, wherein the hydromethanation catalyst comprises at least a portion of the recovered hydromethanation catalyst stream.

12. The process of claim 1, further comprising the steps of:
l) introducing the fines-cleaned methane-enriched raw product gas stream into a heat exchanger unit to remove heat energy and generate a cooled methane-enriched raw product stream;
m) steam shifting a portion of the carbon monoxide in the cooled methane-enriched raw product stream in a shift reactor system to generate a hydrogen-enriched raw product gas stream with a molar ratio of hydrogen to carbon monoxide of close to 3;
n) dehydrating the hydrogen-enriched raw product gas stream in a low-temperature gas cooling system, to generate a dry raw gas stream, the dry raw gas stream comprising carbon dioxide, hydrogen sulfide, hydrogen, carbon monoxide and methane; and
o) removing a substantial portion of the carbon dioxide and a substantial portion of the hydrogen sulfide from the dry raw gas stream in an acid gas removal unit to produce a sweetened gas stream comprising a substantial portion of the hydrogen, carbon monoxide and methane from the dry raw gas stream.

13. The process of claim 12, further comprising the steps of:
p) reacting the carbon monoxide and hydrogen in the sweetened gas stream in a methanation system in the presence of a methanation catalyst to produce heat energy and a pipeline quality substitute natural gas stream;
q) recovering the heat energy from the catalytic methanation system; and
r) utilizing at least a portion of the recovered heat energy to generate and superheat a steam stream.

14. The process of claim 13, wherein the process has a steam demand and a power demand that are met by internal energy integration such that the process requires no net import of steam or power.

* * * * *